(12) United States Patent
Ünlü et al.

(10) Patent No.: US 11,573,177 B2
(45) Date of Patent: Feb. 7, 2023

(54) MULTIPLEXED PHENOTYPING OF NANOVESICLES

(71) Applicant: TRUSTEES OF BOSTON UNIVERSITY, Boston, MA (US)

(72) Inventors: M. Selim Ünlü, Newton, MA (US); George G. Daaboul, Watertown, MA (US); Marcella Chiari, Milan (IT)

(73) Assignee: TRUSTEES OF BOSTON UNIVERSITY, Boston, MA (US)

(*) Notice: Subject to any disclaimer, the term of this patent is extended or adjusted under 35 U.S.C. 154(b) by 153 days.

(21) Appl. No.: 17/148,855

(22) Filed: Jan. 14, 2021

(65) Prior Publication Data

US 2021/0231563 A1 Jul. 29, 2021

Related U.S. Application Data

(63) Continuation of application No. 15/762,290, filed as application No. PCT/US2016/053015 on Sep. 22, 2016, now Pat. No. 10,928,315.

(60) Provisional application No. 62/221,806, filed on Sep. 22, 2015.

(51) Int. Cl.
 *G01N 21/45* (2006.01)
 *G01N 33/543* (2006.01)
 *G01N 21/64* (2006.01)
 *G01N 21/77* (2006.01)

(52) U.S. Cl.
 CPC ......... *G01N 21/45* (2013.01); *G01N 33/5432* (2013.01); *G01N 21/6458* (2013.01); *G01N 2021/6441* (2013.01); *G01N 2021/7779* (2013.01)

(58) Field of Classification Search
None
See application file for complete search history.

(56) References Cited

U.S. PATENT DOCUMENTS

| | | | |
|---|---|---|---|
| 5,482,830 A | 1/1996 | Bogart et al. |
| 5,541,057 A | 7/1996 | Bogart |
| 5,644,388 A | 7/1997 | Maekawa et al. |
| 6,346,376 B1 | 2/2002 | Sigrist et al. |
| 6,878,523 B2 | 4/2005 | Nelson et al. |
| 7,110,118 B2 | 9/2006 | Unlu |
| 7,173,256 B2 | 2/2007 | Fox |
| 7,208,322 B2 | 4/2007 | Stolowitz et al. |

(Continued)

FOREIGN PATENT DOCUMENTS

| | | |
|---|---|---|
| CN | 102460254 A | 5/2012 |
| CN | 102470167 A | 5/2012 |

(Continued)

OTHER PUBLICATIONS

Melo et al. "Glypican-1 identifies cancer exosomes and detects early pancreatic cancer." Nature 523(7559): 177-182 (2015).

(Continued)

*Primary Examiner* — Rebecca M Giere
(74) *Attorney, Agent, or Firm* — Nixon Peabody LLP; Ronald I. Eisenstein; Jeanne Jodoin

(57) ABSTRACT

Provided herein are methods for capturing extracellular vesicles from a biological sample for quantification and/or characterization (e.g., size and/or shape discrimination) using an SP-IRIS system. Also provided herein are methods of detecting a biomarker on captured extracellular vesicles or inside the captured vesicles (e.g., intra-vesicular or intra-exosomal biomarkers).

33 Claims, 7 Drawing Sheets

(56) References Cited

U.S. PATENT DOCUMENTS

| | | |
|---|---|---|
| 7,532,314 B1 | 5/2009 | Black et al. |
| 7,695,680 B2 | 4/2010 | Unlu |
| 7,737,392 B2 | 6/2010 | Cunningham et al. |
| 7,742,622 B2 | 6/2010 | Cunningham et al. |
| 7,742,662 B2 | 6/2010 | Cunningham et al. |
| 7,835,013 B2 | 11/2010 | Jones et al. |
| 7,968,836 B2 | 6/2011 | Cunningham et al. |
| 8,068,995 B2 | 11/2011 | Chau et al. |
| 8,257,936 B2 | 9/2012 | Laing et al. |
| 8,426,028 B2 | 4/2013 | Cai et al. |
| 8,488,120 B2 | 7/2013 | Hall et al. |
| 8,685,755 B2 | 4/2014 | Ferrari et al. |
| 8,830,481 B2 | 9/2014 | Hall et al. |
| 8,841,137 B2 | 9/2014 | Delouise et al. |
| 8,846,129 B2 | 9/2014 | Lin et al. |
| 8,852,876 B2 | 10/2014 | Fang et al. |
| 8,969,509 B2 | 3/2015 | Liu et al. |
| 9,410,949 B2 | 8/2016 | Singamaneni et al. |
| 9,599,611 B2 | 3/2017 | Unlu et al. |
| 9,638,632 B2 | 5/2017 | Bornhop |
| 9,803,236 B2 | 10/2017 | Zhang et al. |
| 9,862,987 B2 | 1/2018 | Lo et al. |
| 10,115,013 B2 | 10/2018 | Sibarita |
| 10,151,680 B2 | 12/2018 | Unlu et al. |
| 2003/0112446 A1 | 6/2003 | Miller et al. |
| 2004/0070764 A1 | 4/2004 | Fujimara et al. |
| 2004/0241176 A1 | 12/2004 | Lamparski et al. |
| 2004/0247485 A1 | 12/2004 | Kraus et al. |
| 2004/0252301 A1 | 12/2004 | Kawano et al. |
| 2005/0130174 A1 | 6/2005 | Bao et al. |
| 2005/0266449 A1 | 12/2005 | Kugler et al. |
| 2006/0014232 A1 | 1/2006 | Inagawa et al. |
| 2006/0063188 A1 | 3/2006 | Zanni et al. |
| 2007/0111224 A1 | 5/2007 | Jung et al. |
| 2007/0211985 A1 | 9/2007 | Duer |
| 2007/0278422 A1 | 12/2007 | Einhorn et al. |
| 2009/0226031 A1 | 9/2009 | Izuka |
| 2010/0021954 A1 | 1/2010 | Deshayes et al. |
| 2010/0145627 A1 | 6/2010 | Wang et al. |
| 2010/0184046 A1 | 7/2010 | Klass et al. |
| 2010/0302544 A1 | 12/2010 | Duer |
| 2011/0091377 A1 | 4/2011 | Alani et al. |
| 2011/0091384 A1 | 4/2011 | Alani et al. |
| 2012/0036702 A1 | 2/2012 | Einhorn et al. |
| 2012/0157350 A1 | 6/2012 | True et al. |
| 2012/0164628 A1 | 6/2012 | Duffin et al. |
| 2012/0208174 A1 | 8/2012 | Galush et al. |
| 2013/0323756 A1 | 12/2013 | Tullis et al. |
| 2014/0377793 A1 | 12/2014 | Bouamrani et al. |
| 2015/0057949 A1 | 2/2015 | Weinberger et al. |
| 2015/0204841 A1 | 6/2015 | Ataullakhanov et al. |
| 2015/0355133 A1 | 12/2015 | Prasad |
| 2016/0017027 A1 | 1/2016 | Azorsa |
| 2016/0257830 A1 | 9/2016 | Singamaneni et al. |
| 2016/0299069 A1 | 10/2016 | Tao et al. |
| 2016/0334398 A1 | 11/2016 | Weissleder et al. |
| 2016/0375439 A1 | 12/2016 | Li et al. |
| 2017/0016821 A1 | 1/2017 | Unlu et al. |
| 2017/0045451 A1 | 2/2017 | Nolan et al. |
| 2017/0067882 A1 | 3/2017 | Bornhop et al. |
| 2017/0116733 A1 | 4/2017 | Juncker et al. |
| 2017/0234801 A1 | 8/2017 | Unlu et al. |
| 2017/0370709 A1 | 12/2017 | Mace et al. |
| 2018/0031483 A1 | 2/2018 | Singamaneni et al. |
| 2018/0052425 A1 | 2/2018 | Ozacan et al. |
| 2018/0106759 A1 | 4/2018 | De Oliveira Botelho et al. |
| 2018/0120302 A1 | 5/2018 | Bornhop |
| 2018/0148714 A1 | 5/2018 | Hadrup et al. |
| 2018/0275097 A1 | 9/2018 | Sandoghdar et al. |
| 2018/0321231 A1 | 11/2018 | Singamaneni et al. |
| 2018/0364270 A1 | 12/2018 | Chiu et al. |
| 2018/0372678 A1 | 12/2018 | Patolsky et al. |
| 2019/0049440 A1 | 2/2019 | Singamaneni et al. |
| 2020/0200740 A1 | 6/2020 | Zafiu et al. |

FOREIGN PATENT DOCUMENTS

| | | |
|---|---|---|
| CN | 102753974 A | 10/2012 |
| EP | 2215470 B1 | 4/2014 |
| WO | 2009048494 A1 | 4/2009 |
| WO | 2009055940 A1 | 5/2009 |
| WO | 2010127001 A1 | 11/2010 |
| WO | 2011000551 A1 | 1/2011 |
| WO | 2011/014282 A2 | 2/2011 |
| WO | 2011014282 A3 | 3/2011 |
| WO | 2011098509 A1 | 8/2011 |
| WO | 2015031694 A2 | 3/2015 |
| WO | 2015038205 A1 | 3/2015 |
| WO | 2015065995 A1 | 5/2015 |
| WO | 2015085096 A1 | 6/2015 |
| WO | 2015134847 A1 | 9/2015 |
| WO | 2016065487 A1 | 5/2016 |
| WO | 2016164124 A1 | 10/2016 |
| WO | 2017053516 A1 | 3/2017 |
| WO | 2017136676 A1 | 8/2017 |
| WO | 2017196823 A1 | 11/2017 |
| WO | 2018094200 A9 | 8/2018 |
| WO | 2018/228625 A1 | 12/2018 |
| WO | 2019/144056 A1 | 7/2019 |
| WO | 2019/222708 A2 | 11/2019 |

OTHER PUBLICATIONS

Avci, O. et al., Interferometric Reflectance Imaging Sensor (IRIS)—A Platform Technology for Multiplexed Diagnostics and Digital Detection, Sensors 15(7):17649-17665 (2015).

Carter, E. P. et al., Visualizing Ebolavirus Particles Using Single-Particle Interferometric Reflectance Imaging Sensor (SP-IRIS), Methods in Molecular Biology, 1628:259-270, (2017).

Chan, S. et al., Nanoscale silicon microcavities for biosensing. Materials Science and Engineering C, 15:277-282, (2001).

Collet, J. et al., The elasticity of an individual fibrin fiber in a clot, PNAS, 102(26):9133-9137, (2005).

Daaboul, G. G. et al., Enhanced light microscopy visualization of virus particles from Zika virus to filamentous ebolaviruses, PLoS One, 12(6):e0179728:1-15, (2017).

Emsley, M. K. et al., Silicon Substrates With Buried Distributed Bragg Reflectors for Resonant Cavity-Enhanced Optoelectronics, IEEE Journal of Selected Topics in Quantum Electronics, 8(4):948-955, (2002).

Gannavarpu, R. et al., Spatiotemporal Characterization of a Fibrin Clot Using Quantitative Phase Imaging, PLOS ONE, 9(11):e111381:1-7, (2014).

Hategan, A. et al., Visualization of the dynamics of fibrin clot growth 1 molecule at a time by total internal reflection fluorescence microscopy, Blood, 121(8):1455-1458, (2013).

Jamur, MC and Oliver C., "Permeabilization of cell membranes," Methods in Molecular Biology, 588:63-66, (2010).

Jenison, R. et al., Interference-based detection of nucleic acid targets on optically coated silicon, Nature Biotechnology, 19:62-65, (2001).

Lancé, Marcus D., A general review of major global coagulation assays: thrombelastography, thrombin generation test and clot waveform analysis, Thrombosis Journal, 13:1-6, (2015).

Lu, J. et al., Reflective Interferometric Detection of Label-Free Oligonucleotides, Analytical Chemistry, 76:4416-4420, (2004).

Matsuura, M. and Kishi, N., Frequency Control Characteristics of a Single-Frequency Fiber Laser with an External Light Injection, IEEE Journal of Selected Topics in Quantum Electronics, 7(1):55-58, (2001).

Moiseev, L. et al., DNA conformation on surfaces measured by fluorescence self-interference, Proceedings of the National Academy of Sciences, 103(8):2623-2628, (2006).

Nikitin, P. I. et al., New direct optical biosensors for multi-analyte detection, Sensors and Actuators B, 90:46-51, (2003).

Piehler, J. et al., Affinity Detection of Low Molecular Weight Analytes, Anal. Chem., 68:139-143, (1996).

Properzi et al., Exosomes: the future of biomarkers in medicine, Biomarkers in Medicine, 84(3):177-189, (2008).

(56) References Cited

OTHER PUBLICATIONS

Rambaran, Roma N. and Serpell, Louise C., Amyloid fibrils, PRION, 2(3):112-117, (2008).
Sandstrom, T. et al., Visual detection of organic monomolecular films by interference colors, Applied Optics, 24:472-479, (1985).
Scherr, S. M. et al., Real-Time Capture and Visualization of Individual Viruses in Complex Media, ACS Nano, 10 (2):2827-2833, (2016).
Su, J. et al., "Label-free detection of single nanoparticles and biological molecules using microtoroid optical Yesonators", Light: Science & Application, 5(1):e16001 (2016).
Thermofisher Scientific, Invitrogen, Alix Polyclonal Antibody, retrieved Feb. 25, 2019 [<https://www.thermofisher.com/antibody/product/Alix-Antibody-Polyclonal/PA5-52873>], 4 pages.
Thermofisher Scientific, Invitrogen, Syndecan 4 Polyclonal Antibody, retrieved Feb. 25, 2019 [<https://www.thermofisher.com/antibody/product/Syndecan-4-Antibody-Polyclonal/36-3100>], 5 pages, (2014).
Van Der Pol, E. et al., Optical and non-optical methods for detection and characterization of microparticles and exosomes, Journal of Thrombosis and Haemostasis, 8(12):2596-2607 (2010).
Wikipedia, Green fluorescent protein, retrieved Feb. 25, 2019, [<https://en.wikipedia.org/wiki/Green_fluorescent_protein>], 19 pages.
Wikipedia, Oligonucleotide, retrieved Feb. 25, 2019, [<https://en.wikipedia.org/wiki/Oligonucleotide>], 4 pages.
Wikipedia, Syntenin-1, 8 pages, retrieved Feb. 25, 2019 [<https://en.wikipedia.org/wiki/Syntenin-1>].
Wikipedia, TSG101, retrieved Feb. 25, 2019, [<https://en.wikipedia.org/wiki/TSG101>], 12 pages.
Yeromonahos, C. et al., Nanostructure of the Fibrin Clot, Biophysical Journal, 99:2018-2027, (2010).
Zarovni N., et al., Integrated isolation and quantitative analysis of exosome shuttled proteins and nucleic acids using immunocapture approaches, Methods, 87:46-58 (2015).
Zhu, L. et al., Label-Free Quantitative Detection of Tumor-Derived Exosomes through Surface Plasmon Resonance Imaging, Analytical Chemistry, 86(17):8857-8864 (2014).
Cretich et al., "Digital detection of biomarkers assisted by nanoparticles: application to diagnostics", Trends in Biotechnology 33:6 343-351 (2015).
Cretich et al., "Silicon biochips for dual label-free and fluorescence detection: Application to protein microarray development", Biosensors and Bioelectronics 26:9 3938-3943 (2011).
Daaboul et al., "High-throughput detection and sizing of individual low-index nanoparticles and viruses for pathogen identification" Nano Letters 10:4727-4731 (2010).
Daaboul et al., "LED-Based interferometric reflectance imaging sensor for quantitative dynamic monitoring of biomolecular interactions" Biosens Bioelectron 26(5): 2221-2227 (2011).
Daaboul, et al., "Digital Sensing and Sizing of Vesicular Stomatitis Virus Pseudotypes in Complex Media; A model for Ebola and Marburg Detection" ACS Nano 8(6):6047-6055 (2014).
Gagni et al., "Combined mass quantitation and phenotyping of intact extracellular vesicles by a microarray platform", Analytica Chimica Acta (02: 160-167 (2015)).
Gong et al., "Microparticles in cancer: A review of recent developments and the potential for clinical application." Seminars in Cell & Developmental Biology, 40:35-40 (2014).
Jorgensen et al., "Extracellular Vesicle (EV) Array: microarray capturing of exosomes and other extracellular vesicles for multiplexed phenotyping" Journal of Extracellular Vesicles, 2:1 1-9 (2013).
Properzi et al., "Exosomes: the future of biomarkers in medicine" Biomark Med, 84(3):177-189 (2008).
Shao et al., "Protein typing of circulating microvesicles allows real-time monitoring of glioblastoma therapy." Nature medicine 18(12):1835 (2012).
Vlassov et al., "Exosomes: current knowledge of their composition, biological functions, and diagnostic and therapeutic potentials." Biochimica et Biophysica Acta (BBA)—General Subjects, 1820(7): 940-948 (2012).
Yurt et al., "Single nanoparticle detectors for biological applications." Nanoscale 4(3): 715-726 (2012).
Reddington et al., "An interferometric reflectance imaging sensor for point of care viral diagnostics." IEEE Transactions on Biomedical Engineering 60.12 (2013): 3276-3283.
Monroe et al., "Single nanoparticle detection for multiplexed protein diagnostics with attomolar sensitivity in serum and unprocessed whole blood." Analytical chemistry 85.7 (2013): 3698-3706.
Rao et al., "Biophysical properties of nucleic acids at surfaces relevant to microarray performance." Biomaterials Science 2.4 (2014): 436-471.
Prestrelski et al., "Dehydration-induced conformational transitions in proteins and their inhibition by stabilizers." Biophysical Journal 65.2 (1993): 661-671.
Cheng et al., "LED-based interferometric reflectance imaging sensor for the detection of amyloid-β aggregation." Analyst 139.1 (2014): 59-65.
Kedersha "Immunofluorescence: Tips for Immunostaining Cultured Cells" (2015) http://www.ptgcn.com/news/blog/immunofluorescence-tips-for-immunostaining-cultured-cells/.
Wang et al., "Local and global anatomy of antibody-protein antigen recognition." Journal of Molecular Recognition 31.5(2018): e2693.
Cretich et al. "Interferometric silicon biochips for label and label-free DNA and protein microarrays." Proteomics 12 (19-20): 2963-2977 (2012).

FIG. 6A
Label-Free SP-IRIS Characterization
FIG. 6B
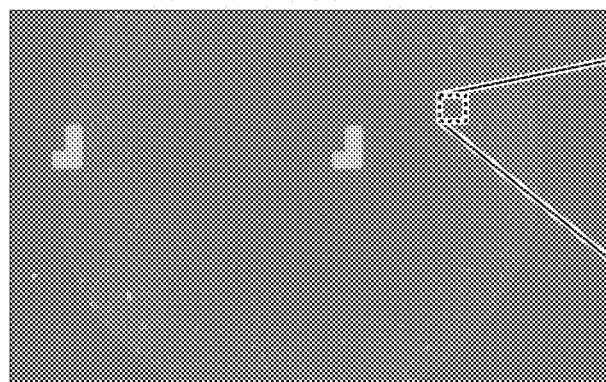
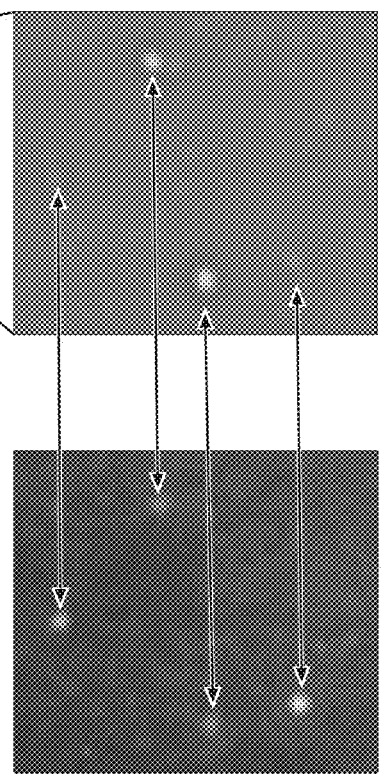
Fluorescent RNA Stain
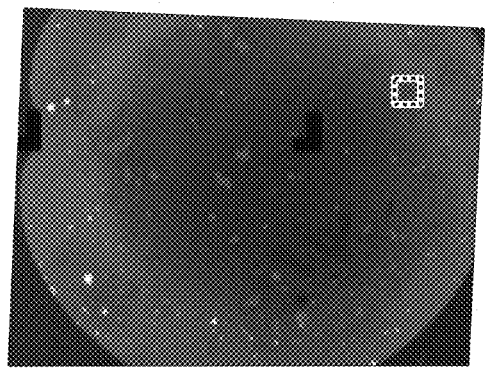
FIG. 6C
FIG. 6D

FIG. 7A
Label-Free SP-IRIS Characterization
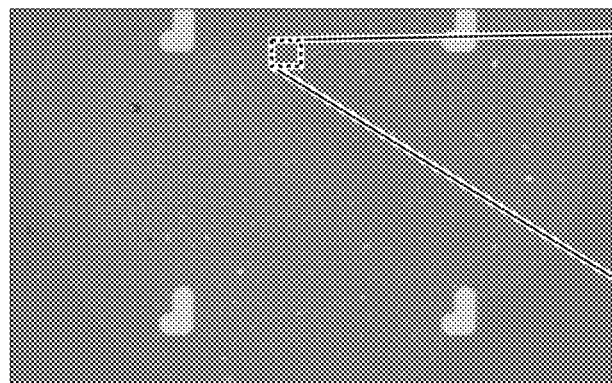
FIG. 7B
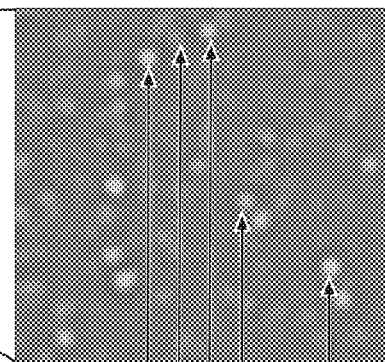
Fluorescent TR ceramide membrane stain
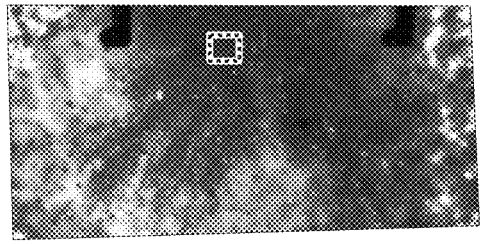
FIG. 7C
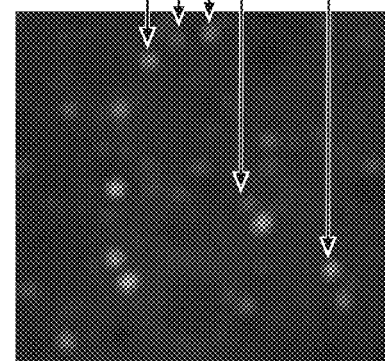
FIG. 7D

MULTIPLEXED PHENOTYPING OF NANOVESICLES

CROSS REFERENCE TO RELATED APPLICATIONS

This application is a Continuation Application of U.S. patent application Ser. No. 15/762,290 filed Mar. 22, 2018, now U.S. Pat. No. 10,928,315 issued Feb. 23, 2021, which is a 35 U.S.C. § 371 National Phase Entry Application of International Application No. PCT/US2016/053015 filed Sep. 22, 2016, which designates the U.S. and which claims benefit under 35 U.S.C. § 119(e) of the U.S. Provisional Application No. 62/221,806 filed Sep. 22, 2015, the contents of each of which are incorporated herein by reference in their entireties.

GOVERNMENT SUPPORT

This invention was made with Government Support under Contract No. AI089673 awarded by the National Institutes of Health. The Government has certain rights in the invention.

FIELD OF THE DISCLOSURE

The present disclosure relates to the quantification and characterization of extracellular vesicles at a single particle level. In some embodiments, the present disclosure further relates to the detection and/or quantification of biomarker expression on the surface of extracellular vesicles or in the intra-vesicular space.

BACKGROUND

High-throughput DNA and protein analysis technologies, such as microarray technologies, are actively being used by biologists and researchers today for high-throughput screening of biomarkers for drug discovery, disease research, and diagnosis. Substrate enhanced microarray imaging has the capability to detect the binding of biomolecules to a surface at tens of thousands of spots simultaneously in a label-free fashion.

The single particle interferometric reflectance imaging sensor (SP-IRIS) system comprises multiple incoherent light sources, such as light-emitting diodes (LEDs), which can be utilized as the illumination source for interferometric principles of detection and measurement. LEDs are very low-cost, compact, and robust, and are thus ideal for large-scale use and distribution for diagnostic and research applications. The SP-IRIS system uses low-cost incoherent illumination sources that enable high magnification detection and imaging of a single biomolecular target in an analyte or sample.

SP-IRIS system is based on imaging reflected light from a sensor surface on which particles of interest are captured. The SP-IRIS sensor is composed of a layered dielectric substrate. The layered structure provides the necessary optical path length difference between the light scattered by the nanoparticle targets and the reference light reflected from the substrate. This SP-IRIS sensor can be made of a variety of dielectric materials such as silicon dioxide on silicon (Si).

SUMMARY

The methods described herein are based, in part, on the discovery that SP-IRIS can be used for the capture of extracellular vesicles from a biological sample on an SP-IRIS sensor, and further permits quantification and characterization of the extracellular vesicles. In addition, the SP-IRIS system can be further employed to detect the presence of a biomarker on the surface of the captured extracellular vesicles or inside the extracellular vesicle (e.g., intra-vesicular or intra-exosomal biomarkers).

Accordingly, provided herein in one aspect is a method for quantifying and/or characterizing extracellular vesicles from a biological sample, the method comprising: (a) contacting an SP-IRIS sensor comprising an extracellular vesicle-specific probe with a biological sample comprising at least one extracellular vesicle, thereby capturing the vesicle(s) on the sensor, (b) contacting the sensor having captured vesicle(s) with a secondary probe comprising a nanoparticle, and (c) imaging the nanoparticle using an SP-IRIS system, thereby quantifying and/or characterizing extracellular vesicles in the biological sample.

In one embodiment of this aspect and all other aspects described herein, the extracellular vesicle-specific probe and/or the secondary probe comprises an antibody.

In another embodiment of this aspect and all other aspects described herein, a plurality of extracellular vesicle-specific probes are contacted with the biological sample to permit isolation and discrimination of particular exosomal populations.

In another embodiment of this aspect and all other aspects provided herein, a plurality of secondary probes are contacted with the sensor having captured vesicle(s) in a multiplex format. The multiplex format permits differential labeling and identification of specific extracellular vesicles and/or their components. In some embodiments, such differential labeling is achieved by using at least two secondary probes (e.g., at least 3, at least 4, at least 5, at least 6, at least 7, at least 8, at least 9, at least 10 or more) that are differentially labeled, e.g., different fluorescent markers, different sized or shaped nanoparticles or gold particles).

In another embodiment of this aspect and all other aspects provided herein, the extracellular vesicles comprise exosomes.

In another embodiment of this aspect and all other aspects provided herein, the captured vesicle(s) are fixed and/or permeabilized on the sensor.

In another embodiment of this aspect and all other aspects provided herein, the secondary probe(s) binds to an intra-vesicular or intra-exosomal marker(s).

In another embodiment of this aspect and all other aspects provided herein, the biological sample comprises a sample obtained from a subject.

In another embodiment of this aspect and all other aspects provided herein, the sample obtained from a subject comprises a blood sample.

In another embodiment of this aspect and all other aspects provided herein, the extracellular vesicle-specific antibody comprises an anti-CD63 antibody. In other embodiments of this aspect and all other aspects provided herein, the extracellular vesicle-specific antibody comprises an anti-CD81, or an anti-CD9 antibody. In another embodiment of this aspect and all other aspects provided herein, at least two extracellular vesicle-specific antibodies are used in combination. For example, a CD63/CD81 antibody combination, a CD63/CD9 antibody combination, or a CD81/CD-9 antibody combination.

In another embodiment of this aspect and all other aspects provided herein, the extracellular vesicle-specific antibody comprises an antibody directed against a biomarker.

In another embodiment of this aspect and all other aspects provided herein, the nanoparticle comprises a gold particle.

In another embodiment of this aspect and all other aspects provided herein, the captured extracellular vesicles are characterized by size and/or shape.

In another embodiment of this aspect and all other aspects provided herein, the sensor further comprises at least one additional extracellular vesicle-specific antibody or a plurality of different extracellular vesicle-specific antibodies for multiplex detection or discrimination of extracellular vesicle populations.

In another embodiment of this aspect and all other aspects provided herein, the plurality of extracellular vesicle-specific antibodies comprises at least 2, at least 5, at least 10, at least 50, at least 100 or more different extracellular vesicle-specific antibodies.

In another embodiment of this aspect and all other aspects provided herein, the multiplex detection further comprises a plurality of secondary probes.

In another embodiment of this aspect and all other aspects provided herein, the plurality of secondary probes are differentially labeled.

In another embodiment of this aspect and all other aspects provided herein, the plurality of secondary probes are differentially labeled with a plurality of nanoparticles that are differentiated by size and/or shape.

In another embodiment of this aspect and all other aspects provided herein, the secondary probe(s) bind to an intra-exosome marker.

Another aspect provided herein relates to an assay for determining the presence of a biomarker on extracellular vesicle(s) from a biological sample in a subject, the assay comprising the steps of: (a) contacting an SP-IRIS sensor comprising a first probe with a biological sample comprising at least one extracellular vesicle, thereby capturing the at least one vesicle on the sensor, (b) imaging the sensor to quantify and individually characterize bound extracellular vesicle(s), (c) contacting the sensor with a second probe comprising a secondary recognition probe that binds a biomarker on the extracellular vesicle conjugated to a label, and (d) imaging the sensor and comparing the image to the image obtained in step (b), wherein a change in the signal imaged in (d) compared to the signal imaged in step (b) indicates the presence of the biomarker on the at least one vesicle.

In one embodiment of this aspect and all other aspects described herein, the at least one extracellular vesicle comprises an exosome.

In another embodiment of this aspect and all other aspects provided herein, the first and/or second probe comprises an antibody.

In another embodiment of this aspect and all other aspects provided herein, the biological sample comprises a sample obtained from a subject.

In another embodiment of this aspect and all other aspects provided herein, the sample obtained from a subject comprises a blood sample.

In another embodiment of this aspect and all other aspects provided herein, the first probe comprises an anti-CD63 antibody. In other embodiments of this aspect and all other aspects provided herein, the extracellular vesicle-specific antibody comprises an anti-CD81, or an anti-CD9 antibody. In another embodiment of this aspect and all other aspects provided herein, at least two extracellular vesicle-specific antibodies are used in combination. For example, a CD63/CD81 antibody combination, a CD63/CD9 antibody combination, or a CD81/CD-9 antibody combination.

In another embodiment of this aspect and all other aspects provided herein, the first and/or second antibody comprises an antibody directed against a biomarker.

In another embodiment of this aspect and all other aspects provided herein, the nanoparticle comprises a gold particle.

In another embodiment of this aspect and all other aspects provided herein, the secondary labeling can be fluorescent using e.g., an antibody attached to a fluorophore or quantum dot.

In another embodiment of this aspect and all other aspects provided herein, the captured extracellular vesicles are characterized by size and/or shape.

In another embodiment of this aspect and all other aspects provided herein, the sensor further comprises at least one additional extracellular vesicle-specific antibody or a plurality of different extracellular vesicle-specific antibodies for multiplex detection or discrimination of extracellular vesicle populations.

In another embodiment of this aspect and all other aspects provided herein, the plurality of extracellular vesicle-specific antibodies comprises at least 2, at least 5, at least 10, at least 50, at least 100 or more different extracellular vesicle-specific antibodies.

In another embodiment of this aspect and all other aspects provided herein, the biomarker is an intra-vesicular or intra-exosomal marker.

In another embodiment of this aspect and all other aspects provided herein, the biomarker is an extra-vesicular or extra-exosomal marker.

In another embodiment of this aspect and all other aspects provided herein, a plurality of secondary probes are used in the method or assay described herein. In another embodiment of this aspect and all other aspects provided herein, the assay is performed in multiplex with differentially labeled secondary recognition probes.

In another embodiment of this aspect and all other aspects provided herein, the plurality of secondary probes are differentially labeled.

In another embodiment of this aspect and all other aspects provided herein, the plurality of secondary probes are differentially labeled with a plurality of nanoparticles that are differentiated by size and/or shape.

Another aspect provided herein relates to a method or assay for label-free detection of extracellular vesicles from a biological sample, the method comprising: (a) contacting an SP-IRIS sensor comprising an extracellular vesicle-specific probe with a biological sample comprising at least one extracellular vesicle, thereby capturing the vesicle(s) on the sensor, (b) imaging the nanoparticle using an SP-IRIS system, thereby detecting extracellular vesicles in the biological sample.

In one embodiment of this aspect and all other aspects provided herein, the method further comprises determining the size, shape and number of the captured extracellular vesicles.

Also provided herein, in another aspect, is a method or assay for detecting extra-vesicular biomarkers on an extracellular vesicle(s) (e.g., one or more individual extracellular vesicle(s)), the method or assay comprising: (a) contacting an SP-IRIS sensor comprising an extracellular vesicle-specific probe with a biological sample comprising at least one extracellular vesicle, thereby capturing the vesicle(s) on the sensor, (b) contacting the sensor having captured vesicle(s) with a secondary probe directed to an extra-vesicular biomarker and further comprising a detectable moiety, and (c) imaging the detectable moiety using an SP-IRIS system, thereby detecting extra-vesicular biomarkers on the extracellular vesicles (e.g., one or more individual extracellular vesicles) in the biological sample.

In one embodiment of this aspect and all other aspects provided herein, the method or assay is performed using a multiplex format.

In another embodiment of this aspect and all other aspects provided herein, the multiplex format comprises the use of a plurality of secondary probes in step (b).

In another embodiment of this aspect and all other aspects provided herein, the plurality of secondary probes are differentially labeled.

In another embodiment of this aspect and all other aspects provided herein, the plurality of secondary probes are differentially labeled with a plurality of nanoparticles that are differentiated by size and/or shape.

Another aspect described herein relates to a method or assay for detecting intra-vesicular biomarkers inside an extracellular vesicle, the method or assay comprising: (a) contacting an SP-IRIS sensor comprising an extracellular vesicle-specific probe with a biological sample comprising at least one extracellular vesicle, thereby capturing the vesicle(s) on the sensor, (b) fixing and/or permeabilizing the captured vesicles from step (a), (c) contacting the sensor having captured vesicle(s) with a secondary probe directed to an intra-vesicular biomarker and further comprising a detectable moiety, and (d) imaging the detectable moiety using an SP-IRIS system, thereby detecting intra-vesicular biomarkers on the extracellular vesicles in the biological sample.

Another aspect provided herein relates to a method for quantifying and/or characterizing extracellular vesicles from a biological sample, the method comprising: (a) contacting an SP-IRIS sensor comprising an extracellular vesicle-specific probe with a biological sample comprising at least one extracellular vesicle, thereby capturing the vesicle(s) on the sensor, (b) imaging the nanoparticle using an SP-IRIS system, thereby quantifying and/or characterizing extracellular vesicles in the biological sample.

Also provided herein, in another aspect is a method for quantifying and/or characterizing extracellular vesicles from a biological sample, the method comprising: (a) contacting an SP-IRIS sensor comprising an extracellular vesicle-specific probe with a biological sample comprising at least one extracellular vesicle, thereby capturing the vesicle(s) on the sensor, (b) contacting the sensor having captured vesicle(s) with a secondary probe tagged with a fluorescent tag or a quantum dot, and (c) imaging the fluorescent tag or quantum dot using an SP-IRIS system, thereby quantifying and/or characterizing extracellular vesicles in the biological sample.

Another aspect provided herein relates to a method for quantifying and/or characterizing extracellular vesicles in a population that express a biomarker, the method comprising: (a) contacting a biological sample comprising at least one extracellular vesicle with one or more differentially labeled probes that bind one or more biomarkers, (b) contacting an SP-IRIS sensor comprising an extracellular vesicle-specific probe with the labeled biological sample of step (a), thereby capturing a population of extracellular vesicle(s) from the labeled biological sample of step (a) on the sensor, (c) imaging the captured extracellular vesicle(s) of step (b) using an SP-IRIS system, thereby quantifying and/or characterizing extracellular vesicles in the biological sample, (d) imaging the one or more differentially labeled probes using an SP-IRIS system, thereby quantifying and/or characterizing the extracellular vesicles labeled with the one or more differentially labeled probes in the biological sample, and (e) comparing the image obtained in step (d) with the image obtained in step (c) to quantify and/or characterize the extracellular vesicles expressing the one or more biomarkers in the population of extracellular vesicles captured in step (b).

BRIEF DESCRIPTION OF THE FIGURES

FIG. 3A, an expected particle response from SP-IRIS for two wavelengths of light ($\lambda=525$ nm and $\lambda=625$ nm). FIG. 3B, Example image of heterogeneous sized particles.

FIGS. 6A-6D Exosomes from Panc-1 cell culture media were contacted with the SP-IRIS sensor surface functionalized with exosome specific probes. FIG. 6A shows a label-free SP-IRIS image of the captured vesicles on the probes spot. FIG. 6B is a small inset of the label-free SP-IRIS image. The label-free SP-IRIS image allows detection of the vesicles and determination of size. FIG. 6C is a fluorescent image taken on the identical spot after incubating the SP-IRIS sensor with SYTO RNA Select cell stain from Molecular Probes™. FIG. 6D shows a small inset of the fluorescent image for comparison with the label-free SP-IRIS image in FIG. 6B. By comparing the two images one can see that only some of the vesicles in the population contain RNA. The arrows help guide the reader in the comparison of the two images in FIGS. 6B and 6D.

FIGS. 7A-7D Exosomes from Panc-1 cell culture media were contacted with the SP-IRIS sensor surface functionalized with exosome specific probes. FIG. 7A shows a label-free SP-IRIS image of the captured vesicles on the probes spot. FIG. 7B shows a small inset of the label-free SP-IRIS image. The label-free SP-IRIS image allows detection of the vesicles and determination of size.

FIG. 7C is a fluorescent image taken on the identical spot after incubating the SP-IRIS sensor with BODIPY TR Ceramide membrane stain from Molecular Probes™. FIG. 7D shows a small inset of the fluorescent image for comparison with the label-free SP-IRIS image in FIG. 7B. By comparing the two images one can see that most of the detected vesicles label-free contain a lipid as shown by the fluorescent images. The arrows help guide the reader in the comparison of the two images.

DETAILED DESCRIPTION

Figure 1:
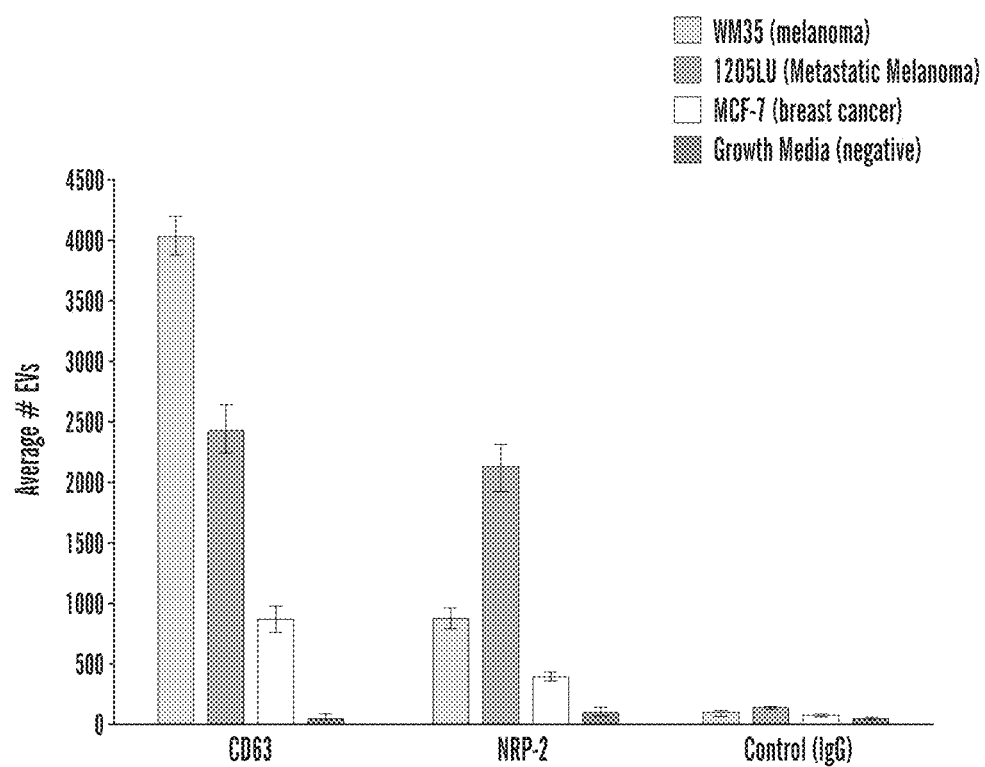
FIG. 1 shows extracellular vesicle detection from different cell-lines.

Provided herein are methods for capturing extracellular vesicles from a biological sample for quantification and/or characterization (e.g., size and/or shape discrimination) using an SP-IRIS system. Also provided herein are methods of detecting a biomarker on captured extracellular vesicles or inside the captured vesicles (e.g., intra-vesicular or intra-exosomal biomarkers).

Definitions

As used herein, the term "sample" refers to a sample comprising at least one extracellular vesicle. In one embodiment, a "biological sample," as that term is used herein, refers to a sample obtained from a subject, wherein the sample comprises at least one extracellular vesicle. While not necessary or required, the term "biological sample" is intended to encompass samples that are processed prior to imaging using the systems and methods described herein. For example, a biological sample can be a whole blood sample obtained from a subject, or can be further processed to a serum sample, a platelet sample, an exosome sample, etc.

As used herein, the term "subject" refers to a plant or animal, particularly a human, from which a biological sample is obtained or derived from. The term "subject" as used herein encompasses both human and non-human animals. The term "non-human animals" includes all vertebrates, e.g., mammals, such as non-human primates, (particularly higher primates), sheep, dog, rodent (e.g., mouse or rat), guinea pig, goat, pig, cat, rabbits, cows, and non-mammals such as chickens, amphibians, reptiles etc. In one embodiment, the subject is human. In another embodiment, the subject is an experimental animal or animal substitute as a disease model. In some embodiments, the term "subject" refers to a mammal, including, but not limited to, murines, simians, humans, felines, canines, equines, bovines, mammalian farm animals, mammalian sport animals, and mammalian pets. In one embodiment, the subject is a human subject.

As used herein, the term "extracellular vesicle" refers to substantially spherical bodies or membranous bodies from 1 nm-999 µm in size, such as e.g., liposomes, micelles, exosomes, microbubbles, or unilamellar vesicles. In some embodiments, the particle is less than 900 µm, less than 800 µm, less than 700 µm, less than 600 µm, less than 500 µm, less than 400 µm, less than 300 µm, less than 200 µm, less than 100 µm, less than 90 µm, less than 80 µm, less than 75 µm, less than 70 µm, less than 60 µm, less than 50 µm, less than 40 µm, less than 30 µm, less than 25 µm, less than 20 µm, less than 15 µm, less than 10 µm, less than 5 µm, less than 2 µm, less than 1 µm, less than 750 nm, less than 500 nm, less than 400 nm, less than 300 nm, less than 200 nm, less than 100 nm, less than 50 nm, less than 40 nm, less than 30 nm, less than 20 nm, less than 10 nm, less than 5 nm, or smaller.

As used herein, the term "individually characterize," when used in reference to extracellular vesicles bound to an SP-IRIS sensor, refers to the characterization of size, shape, density, area, or other phenotypic measure of a single extracellular vesicle.

As used herein, the term "secondary recognition probe" refers to a second probe that binds a biomarker in or on the extracellular vesicle. In some embodiments, the secondary recognition probe can also bind an unlabeled first antibody probe to permit detection of binding of the first antibody. Such a method is analogous to the use of a secondary antibody in an ELISA method.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g., the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase" or "enhance" or "activate" are all used herein to generally mean an increase by a statically significant amount; for the avoidance of any doubt, the terms "increased", "increase" or "enhance" or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, at least about a 20-fold increase, at least about a 50-fold increase, at least about a 100-fold increase, at least about a 1000-fold increase or more as compared to a reference level.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular.

Other than in the operating examples, or where otherwise indicated, all numbers expressing quantities of ingredients or reaction conditions used herein should be understood as modified in all instances by the term "about." The term "about" when used in connection with percentages can mean±1%.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in molecular biology can be found in The Merck Manual of Diagnosis and Therapy, 19th Edition, published by Merck Sharp & Dohme Corp., 2011 (ISBN 978-0-911910-19-3); Robert S. Porter et al. (eds.), The Encyclopedia of Molecular Cell Biology and Molecular Medicine, published by Blackwell Science Ltd., 1999-2012 (ISBN 9783527600908); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006; Lewin's Genes XI, published by Jones & Bartlett Publishers, 2014 (ISBN-1449659055); Michael Richard Green and Joseph Sambrook, Molecular Cloning: A Laboratory Manual, 4th ed., Cold Spring Harbor Laboratory Press, Cold Spring Harbor, N.Y., USA (2012) (ISBN 1936113414); Davis et al., Basic Methods in Molecular Biology, Elsevier Science Publishing, Inc., New York, USA (2012) (ISBN 044460149X); Laboratory Methods in Enzymology: DNA, Jon Lorsch (ed.) Elsevier, 2013 (ISBN 0124199542); Current Protocols in Molecular Biology (CPMB), Frederick M. Ausubel (ed.), John Wiley and Sons, 2014 (ISBN 047150338X, 9780471503385), and Current Protocols in Protein Science (CPPS), John E. Coligan (ed.), John Wiley and Sons, Inc., 2005 (ISBN 0471142735), the contents of which are all incorporated by reference herein in their entireties.

Cancer & Disease Monitoring and Treatment

Cancer disease monitoring and treatment is at the forefront of personalized medicine. Cancer therapies are being developed to allow more precise targeting of the cancer while minimizing the adverse effects on healthy cells in a patient. Specific targeted therapy is challenging because there needs to be a continuous monitoring of the status of the disease during treatment. Currently, disease monitoring requires repeated tissue biopsies to track the molecular signatures or biomarkers. However, tissue biopsies are invasive and carry a risk of complications. Less invasive methods like fine needle biopsies are not ideal because they sample a very small portion of the tumor, missing any heterogeneity. Non-invasive imaging techniques like computed tomography scans (CT-scans) are used to monitor tumor size/burden, which reflects treatment efficacy. CT-scans cannot resolve small changes, therefore physicians cannot identify effectiveness of treatment for weeks or months. Also, CT-scans cannot be performed frequently because of radiation risks. There is a need for less-invasive monitoring techniques to improve cancer therapies.

To overcome the cost and invasiveness associated with tissue biopsies, it has been shown over the last decade that circulating tumor cells (CTCs) and circulating tumor DNA (ctDNA) can be found in blood and other biological fluids (see e.g., Alix-Panabieres and Pantel. (2013) Clin Chem 59(1):110-118; Bettegowda et al. (2014) Sci Transl Med 6(224):224ra24; Diaz and Bardelli. (2014) J Clin Oncol 32(6):579-586). These methods show promise to reveal the molecular makeup of the cancer using less invasive samples like blood, serum, urine, and saliva. These methods are termed "liquid-biopsy" because they aim to provide similar results to a tissue biopsy while allowing near continuous monitoring of a patients cancer progression and molecular makeup of the cancer cells. There has been significant technology development around being able to isolate (Ozkumur et al. (2013) Sci Transl Med 5(179):179ra47; Karabacak et al. (2014) Nat Protoc 9(3):694-710) and detect (Castro et al. (2014) Lab chip 14(1):14-23) CTCs because CTCs are found at very low concentrations of about one in a billion cells. ctDNA are more abundant in absolute number, however they are in a fluid with a high concentration of normal DNA. Recently, improvements in nucleic acid sequencing and mutation detection have enabled the use of ctDNA (Bettegowda et al. (2014) Sci Transl Med 6(224): 224ra24; Dawson et al. (2013) N Engl J Med 368(13): 1199-1209).

While CTC and ctDNA technologies are being developed for oncology applications, it has been shown that a third set of circulating biomarkers, extracellular vesicles (EVs), are also shed into the circulation from cancer cells (Revenfeld et al. (2014) Clin Ther 36(6):830-846; Yang et al. (2014) PLoS ONE 9(11):e110641). EVs are lipid vesicles that are released from cells and can be found in body fluids. These EVs can share the same surface markers and internal molecular markers (e.g., proteins, mRNA, and miRNA) as their parent cell. It has been proposed that a cancer cell can shed a much higher concentration of EVs per cell (Taylor and Gercel-Taylor. (2008) Gynecol Oncol 110(1):13-21; Riches et al. (2014) 50(5):1025-1034), which makes them more abundant than CTCs. The higher concentration of exosomes can make early detection possible and also provide phenotypic information from the parent tumor cells. Thus, EVs can play a role in treatment, monitoring, and companion diagnostics. A recent study showed that EVs can serve as a companion diagnostic (cDx) for Cetuximab (Erbitux) since the EVs carry the drug target epidermal growth factor and the mutated KRAS gene, which correlates with poor therapeutic response (Yamashita et al. (2013) Phar-In J Pharm Sci 68(12): 969-973; Kahlert et al. (2014) J Biol Chem 289(7): 3869-3875). Since the discovery of EVs more than 40 years ago (Crawford, N. (1971) Br J Haematol 21(1):53-69) the field has seen a strong resurgence recently (Caby, M P. (2005) In Immunol 17(7):879-887; van Niel, G. (2006) J Biochem (Tokyo) 140(1):13-21; Simpson, et al. (2008) 8(19):4083-4099 with EVs being studied in many oncology areas (Katsuda et al. (2014) Proteomics 14(4-5):412-425; Thery et al. (2009) Nat Rev Immunol 9(8):581-593). In recent studies, EVs have been shown to play a role in cell-cell communications (Thery et al. (2009) Nat Rev Immunol 9(8):581-593; Ratajcxak et al. (2006) Leukemia 20(9):1487-1495), extracellular matrix degradation (Inder et al. (2014) J Extracell Vesicles vol. 3; Cocucci and Meldolesi. (2015) Trends Cell Biol 25(6):364-372), tumor growth and metastasis (Logozzi et al. (2009) PLoS ONE 4(4):e5219; Peinado et al. (2012) Nat Med 18(6):883-891), and resistance to drugs (Gong et al. (2012) Cancer Treat Rev 38(3): 226-234). Since EVs are more abundant than CTCs there has been interest in screening EVs from bodily fluids for early diagnosis (Vlassov et al. (2012) Biochim Biophys Acta BBA 1820(7):940-948), progression/recurrence monitoring (Shao et al. (2012) Nat Med 18(12):1835-1840; Gong et al. (2014) Semin Cell Dev Biol 40:35-40), and determination of drug treatment (Shao et al. (2012) Nat Med 18(12):1835-1840).

EVs consist of a diverse population formed through different mechanisms (van der Pol et al. (2012) Pharmacol Rev 64(3):676-705; Andaloussi et al. (2013) Nat Rev Drug Discov 12(5):347-357; Gyorgy et al. (2011) Cell Mol Life Sci 68(16):2667-2688). EVs can be split into three types: exosomes, microvesicles, and apoptotic bodies. Exosomes are secreted from multivesicular endosomes after fusion with the plasma membrane and are 40-200 nm in diameter. Microvesicles are formed from budding of the plasma membrane of cells and are 50-1,000 nm in diameter. Apoptotic bodies are generated from cell disintegration and have the largest size range of 50-5,000 nm. Exosomes can usually be differentiated from other EVs by the presence of scaffolding proteins like tetraspanins (e.g., CD63, CD81, and CD9).

The use of EVs is contemplated for the detection and/or prognosis of a variety of diseases and is not strictly limited to the detection and/or prognosis of cancer. For example, the detection and/or prognosis of a variety of neurodegenerative diseases, infectious disease and cardiovascular disease can also be determined. Examples of cancers that can be detected or monitored using the methods described herein include, but are not limited to, carcinoma, lymphoma, blastoma, sarcoma, and leukemia or lymphoid malignancies. More particular examples of such cancers are noted below and include: squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial cancer or uterine carcinoma, salivary gland carcinoma, kidney or renal cancer, prostate cancer, vulvar cancer, thyroid cancer, hepatic carcinoma, anal carcinoma, penile carcinoma, as well as head and neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

In some embodiments, the cancer is an adenocarcinoma. In some embodiments, the cancer is selected from breast, lung, head or neck, prostate, esophageal, tracheal, brain, liver, bladder, stomach, pancreatic, ovarian, uterine, cervical, testicular, colon, rectal, and skin. In some embodiments the cancer is an adenocarcinoma of the breast, lung, head or neck, prostate, esophagus, trachea, brain, liver, bladder, stomach, pancreas, ovary, uterus cervix, testicular, colon, rectum, or skin. In some embodiments the cancer is selected from pancreatic, lung (e.g., small cell or non-small cell), and breast.

Neurodegenerative diseases that can be detected using EVs include, for example, Alzheimer's disease, Chronic traumatic encephalopathy, Huntington's disease, Parkinson's Disease, and Prion's Diseases.

TABLE 1

Cancers and Associated EV biomarkers

| Cancer | Markers |
| --- | --- |
| Ovarian | L1CAM, CD24, EMMPRIN TGFβ1, MAGE3/6 Claudin-4 |
| Glioblastoma | EGFRvIII, EGFR, PDPN IDH1 |
| Melanoma | CD63 and Caveolin-1 |
| Oral | FasL |
| Gastric | Her-2/neu, CCR6 |
| Bladder | EDIL-3 LASS2, GALNT1 |
| Kidney | MMP-9, ceruloplasmin, PODXL, DKK4, CAIX |
| Prostate | ITGA3, ITGB1 CDCP1, CD151, CD147 |
| Lung | EGFR |
| Pancreas | Apbb1ip, Aspn, CO31781, Daf2, Foxp1, Gng2 CD44v6, Tspan8, EpCam, MET, CD104 |
| Leukemia | CD34 |

Biological Samples

Essentially any sample can be tested using the methods and systems described herein, provided that the sample comprises at least one extracellular vesicle (e.g., an exosome). The term "biological sample" can refer to any sample containing an extracellular vesicle, such as, for example, blood, plasma, serum, urine, gastrointestinal secretions, homogenates of tissues or tumors, circulating cells and cell particles (e.g., circulating tumor cells), synovial fluid, feces, saliva, sputum, cyst fluid, amniotic fluid, cerebrospinal fluid, peritoneal fluid, lung lavage fluid, semen, lymphatic fluid, tears, prostate fluid, cell culture media, or cellular lysates. A sample can also be obtained from an environmental source, such as water sample obtained from a polluted lake or other body of water, a liquid sample obtained from a food source believed to be contaminated, or a plant sample.

A significant advantage of the SP-IRIS system for quantification and/or characterization (e.g., size and/or shape discrimination) of extracellular vesicles is that there is no need to isolate or enrich the extracellular vesicles from the biological sample prior to performing the methods described herein. For example, when quantifying and/or characterizing circulating exosomes from whole blood, no prior isolation step is required and the blood sample can simply be contacted with the SP-IRIS sensor. Therefore, in one embodiment, the method does not comprise a step of isolating extracellular vesicles (e.g., exosomes) from the biological sample. In another embodiment, the method does not comprise a step of enriching extracellular vesicles (e.g., exosomes) in a biological sample.

Exosomes

Exosomes are cell-derived nanovesicles of 30-200 nm diameters that are released from most living cells. Exosomes are present in virtually all biological fluids of the body, including blood and urine (8, 9). Exosomes were first identified in the harvested media of reticulocyte cell cultures as microvesicles containing membrane proteins, including the transferrin receptor (10). Since then, several cell types have been described to release exosomes into the extracellular environment. Exosomes are formed by membrane invagination of late endosomes, resulting in the vesicles containing some cytosolic components and extracellular domains of plasma membrane receptors of cells. Exosomes are released into the extracellular environment from cells following the fusion of late endosomal multivesicular bodies (MVBs) with the plasma membrane (11, 12), or they may be released from the plasma membrane directly (13). Because of their intracellular origin, exosomes harbor specific protein markers of the endosomal pathway, such as tetraspanins (CD63, CD9 and CD81) and heat shock proteins (HSP70), which are not found in other types of nanovesicles of similar size (9, 14). It is becoming increasingly clear that exosomes have specialized functions and play key roles in such processes as, coagulation, intercellular signaling, and waste management (12). Consequently, there is a growing interest in the clinical applications of exosomes.

Typically, exosomes in the size range of 40 nm-100 nm can be counted and/or sized with the methods described herein, however exosomes or other extracellular vesicles up to 150 nm can also be characterized as described herein. Extracellular vesicles contemplated for quantification and/or characterization using the methods and systems described herein can be at least 15 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 75 nm, at least 80 nm, at least 85 nm, at least 90 nm, at least 95 nm, at least 100 nm, at least 125 nm, at least 150 nm, or more. In some embodiments, the extracellular vesicles are less than 150 nm, less than 125 nm, less than 100 nm, less than 95 nm, less than 90 nm, less than 85 nm, less than 80 nm, less than 75 nm, less than 70 nm, less than 65 nm, less than 60 nm, less than 55 nm, less than 50 nm, less than 45 nm, less than 40 nm, less than 35 nm, less than 30 nm, less than 25 nm, less than 20 nm, or smaller. In certain embodiments, the extracellular vesicles are between 15-200 nm, 30-200 nm, 50-200 nm, 75-200 nm, 100-200 nm, 125-200 nm, 150-200 nm, 175-200 nm, 15-25 nm, 15-50 nm, 15-75 nm, 15-100 nm, 15-125 nm, 15-150 nm, 15-175 nm, 30-100 nm, 40-100 nm, 50-100 nm, 60-100 nm, 70-100 nm, 80-100 nm, 40-80 nm, 40-60 nm, 30-60 nm, 30-50 nm, or any range therebetween.

In some embodiments, the extracellular vesicles can be discriminated by shape using the methods described herein. For example, extracellular vesicles can be the following shapes: perfectly spherical, substantially spherical, elliptical, oblong, teardrop, dome, button, non-axisymmetric, among others.

SP-IRIS Detection System

DNA and protein microarrays are now ubiquitous tools of medical research because they enable highly multiplexed assays to be performed quickly and cheaply with little specialized knowledge. However, polymerase chain reaction (PCR) (in the case of nucleic acid detection) and ELISA or luminescence immunoassay (in the case of protein and small molecules) still provide the gold standard in sensitivity and selectivity and therefore continue to be favored despite meager multiplexing and labor intensiveness of sample preparation. The problem of enhancing the sensitivity of microarray-format assays has been approached a variety of ways, the most successful of which have been optical scattering (15-17), or electrochemical (18, 19) techniques. Beyond the realm of microarray sensors, techniques utilizing hydrogel microparticles with shape labeling (20) and nanoparticles with DNA barcodes (15, 16) have been developed to provide a degree of multiplexing to highly sensitive detection platforms, which have their own sets of drawbacks associated with assay complexity. Regardless, none of these technologies has achieved the simplicity, speed, and performance required to replace current commercial amplification- or enzyme-based protocols. Thus, there is a need for a system which can sufficiently enhance the sensitivity of microarray based technologies such that its inherent advantages in simplicity and multiplexing may be utilized.

To the inventors' knowledge there is no highly multiplexed method that can detect and size/shape individual nanovesicles on a capture surface in a microarray format. SP-IRIS technology developed by the Unlu Lab at Boston University (see e.g., WO2011/014282, the contents of which are incorporated herein by reference in their entirety) allows labeled and label-free detection of individual captured nanovesicles on the sensor's surface that can be tiled with many capture probes (i.e., antibodies, peptides, glycans, DNA oligos, aptamers, etc.) in a microarray format. The signal in the SP-IRIS image of the detected nanovesicles can then be used to size and/or shape the nanovesicles. The principle of detection for SP-IRIS is based on the enhanced contrast in the scattering signal from particles on a layered substrate.

To detect and size/shape nanoparticles, SP-IRIS shines light from visible LED sources on nanoparticles bound to the sensor surface, which consists of a silicon dioxide layer on top of a silicon substrate. Interference of light reflected from the sensor surface is modified by the presence of particles producing a distinct signal that reveals the size and/or shape of the particle. In the inventors' approach the dielectric layered structure acts as an optical antenna optimizing the elastic scattering characteristics of nanoparticles for sensitive detection and analysis. The inventors have successfully detected low-index dielectric particles with diameters of 60 nm to 200 nm and metallic (Au and Ag) nanoparticles with diameters 20 nm to 100 nm (21). The simultaneous detection of multiple viruses in serum or whole blood as well as in samples contaminated with high levels of bacteria (22) has been performed using this approach. By employing affinity-based capture, size and/or shape discrimination, and a "digital" detection scheme to count single virus particles, the SP-IRIS system is shown to be a robust and sensitive virus sensing assay that can been established for targets in complex samples.

Further, in some embodiments, the SP-IRIS sensors can be used to detect a change in interference pattern at one or more distinct locations on the sensor substrate. For example, when the sensor is used to identify biomolecular targets on an extracellular vesicle, the captured extracellular vesicles can be contacted with a probe directed to a desired biomarker in one or more distinct locations on the sensor substrate surface. The optical interference pattern of the one or more distinct locations is then detected and compared to the initial optical interference pattern. The shift in optical interference pattern observed between the initial capture of the extracellular vesicles and the image obtained after contacting with a biomarker-specific binding agent is indicative of the biomarker expression level and/or number of extracellular vesicles expressing the biomarker.

As used herein, the term "SP-IRIS sensor" is used to refer to a substrate that is functionalized with at least one probe and permits imaging using the SP-IRIS system. Typically, the sensor comprises a silicon (Si) wafer layered with silicon dioxide ($SiO_2$), however other substrates can be substituted provided that they permit substantially similar results as the $Si/SiO_2$ sensor using the SP-IRIS system. In some embodiments, the SP-IRIS sensor comprises a microarray.

In some embodiments of the aspects described herein, the microarray is fabricated on a layered substrate comprising 100 nm-1000 nm of $SiO_2$ layered on a Si wafer. That is, the sensor comprises a substrate comprising 100 nm-1000 nm of $SiO_2$ layered on a Si wafer and further comprising at least one probe. In some embodiments of this aspect, the microarray is fabricated on a layered substrate comprising at least 100 nm of $SiO_2$ layered on a Si wafer. In some embodiments of this aspect, the microarray is fabricated on a layered substrate comprising at least 200 nm of $SiO_2$ layered on a Si wafer. In some embodiments of this aspect, the microarray is fabricated on a layered substrate comprising at least 300 nm of $SiO_2$ layered on a Si wafer. In some embodiments of this aspect, the microarray is fabricated on a layered substrate comprising at least 400 nm of $SiO_2$ layered on a Si wafer. In some embodiments of this aspect, the microarray is fabricated on a layered substrate comprising at least 500 nm of $SiO_2$ layered on a Si wafer. In some embodiments of this aspect, the microarray is fabricated on a layered substrate comprising at least 600 nm of $SiO_2$ layered on a Si wafer. In some embodiments of this aspect, the microarray is fabricated on a layered substrate comprising at least 700 nm of $SiO_2$ layered on a Si wafer. In some embodiments of this aspect, the microarray is fabricated on a layered substrate comprising at least 800 nm of $SiO_2$ layered on a Si wafer. In some embodiments of this aspect, the microarray is fabricated on a layered substrate comprising at least 900 nm of $SiO_2$ layered on a Si wafer. In some embodiments of this aspect, the microarray is fabricated on a layered substrate comprising at least 1000 nm of $SiO_2$ layered on a Si wafer.

The sensors used with the methods described herein can comprise one or more of a plurality of immobilized probes attached to the substrate layer. For example, one or more specific immobilized probes can be arranged in an array of one or more distinct locations on the surface of the biosensor. The one or more distinct locations can define microarray spots of about 50-500 microns, or about 150-200 microns in diameter.

In some embodiments, the immobilized probes can be a DNA oligonucleotide, RNA oligonucleotide, a peptide, a protein, such as a transcription factor, antibody or enzyme, a small organic molecule, or any combination therein. Such biosensors are useful for the detection of biomolecular interactions, including, but not limited to, DNA-DNA, DNA-RNA, DNA-protein, RNA-RNA, RNA-protein, and protein-protein interactions.

As used herein, a probe immobilized on the substrate surface of a biosensor can be, for example, an organic molecule, such as a nucleic acid, oligonucleotide, peptide, polypeptide, antigen, polyclonal antibody, monoclonal antibody, single chain antibody (scFv), F(ab) fragment, F(ab') 2 fragment, Fv fragment, small organic molecule, polymer, compounds from a combinatorial chemical library, inorganic molecule, or any combination therein.

In some embodiments, the SP-IRIS system is configured for label-free detection of an extracellular vesicle. In other embodiments, the SP-IRIS system is configured for labeled detection of an extracellular vesicle by indirectly imaging a nanoparticle, such as a gold particle, or a fluorescent moiety. As used herein, the term "nanoparticle," as defined herein, refers to any target to be detected by the biosensors and methods described herein that has a radius of up to 999 nm. For example, a nanoparticle can be 1 nm-999 nm, 1 nm-900 nm, 1 nm-800 nm, 1 nm-700 nm, 1 nm-600 nm, 1 nm-500 nm, 1 nm-400 nm, 1 nm-300 nm, 1 nm-200 nm, 1 nm-150 nm, 1 nm-100 nm, 1 nm-75 nm, 1 nm-50 nm, 1 nm-25 nm, 1 nm-20 nm, 1 nm-10 nm, 1 nm-5 nm, 1 nm-2.5 nm, 500 nm-999 nm, 600 nm-999 nm, 700 nm-999 nm, 800 nm-999 nm, 900 nm-999 nm, 100 nm-500 nm, 100 nm-400 nm, 100 nm-300 nm, 100 nm-200 nm or any range between. In some embodiments, the radii is at least 2.5 nm, at least 5 nm, at least 10 nm, at least 15 nm, at least 20 nm, at least 25 nm, at least 30 nm, at least 35 nm, at least 40 nm, at least 45 nm, at least 50 nm, at least 55 nm, at least 60 nm, at least 65 nm, at least 70 nm, at least 80 nm, at least 85 nm, at least 90 nm, at least 95 nm, at least 100 nm, at least 125 nm, at least 150 nm, at least 200 nm, at least 300 nm, at least 400 nm, at least 500 nm or more. It is to be understood that a nanoparticle can have a variety of shapes, e.g., may not have a perfectly spherical shape, but can also be ellipsoid, rod-shaped, hexahedral, polyhedral, cuboid, or any such shape in which at least one dimension corresponds to the measurements described herein. In some embodiments, different shaped nanoparticles can be used.

In some embodiments, secondary labeling employs fluorescence labeling, for example, by using an antibody attached to a fluorophore or quantum dot. Such fluorescent methods provide an additional advantage that from the first contact with the sensor, one can detect, count, and size/shape the extracellular vesicles (EVs) label-free. The labeling of the EVs can either be through a nanoparticle tagged probe (e.g., an antibody) or a fluorescently tagged approach. In some embodiments, the second fluorescent detection modality is built into the SP-IRIS microscope.

Multiplex SP-IRIS: The SP-IRIS system can be used to study one or a number of specific binding interactions in parallel, i.e., multiplex applications. Binding of one or more specific binding substances to their respective binding molecules can be detected, without the use of labels, by applying a sample comprising one or more extracellular vesicles to an SP-IRIS sensor that has one or more specific binding molecules immobilized on its surface. The SP-IRIS sensor is illuminated with light, and if one or more extracellular vesicles in the sample specifically bind one or more of the immobilized molecules, a phase-shift in the interference pattern occurs relative to the interference pattern when one or more specific extracellular vesicles have not bound to the immobilized binding molecules. In those embodiments where a sensor substrate surface comprises an array of one or more distinct locations comprising one or more specific immobilized binding molecules, then the interference pattern is detected from each distinct location of the biosensor.

Thus, in some embodiments, a variety of specific binding molecules, for example, antibodies, can be immobilized in an array format onto the substrate surface of an SP-IRIS sensor. The sensor is then contacted with a test sample of interest comprising potential extracellular vesicle binding partners, such as proteins. Only the proteins that specifically bind to the antibodies immobilized on the sensor remain bound to the sensor. Such an approach is essentially a large-scale version of an enzyme-linked immunosorbent assay; however, the use of an enzyme or fluorescent label is not required. For high-throughput applications, sensors can be arranged in an array of arrays, wherein several sensors comprising an array of specific binding molecules on the substrate surface are arranged in an array.

Accordingly, in other embodiments of this aspect and all such aspects described herein, sensors are used to detect binding of one or more of a plurality of extracellular vesicles present in a sample to a biosensor substrate layer comprising one or more of a plurality of immobilized molecules attached to the substrate layer. For example, one or more specific immobilized molecules can be arranged in an array of one or more distinct locations on the surface of the sensor.

In some embodiments, the term "multiplex" refers to the detection of less than 1500 different biomarkers (e.g., protein biomarkers, miRNA biomarkers etc.) in a single sample or at a single time. In other embodiments, "multiplex" refers to the detection of less than 1000, less than 900, less than 800, less than 700, less than 600, less than 500, less than 400, less than 300, less than 200, less than 100, less than 50, less than 40, less than 30, less than 20, less than 10, or less than 5 different protein or polynucleotide markers simultaneously or in parallel.

Advantages of the SP-IRIS System for Exosomal Characterization

Conventional extracellular vesicle detection techniques for monitoring diseases, such as cancer, are limited in their ability to detect EVs without the need for enrichment of vesicles in the sample. Thus, conventional EV detection techniques can measure only (i) phenotype, or (ii) size, shape and enumeration. The SP-IRIS system has several advantages over such conventional techniques:

1. The SP-IRIS system permits sensitive detection and sizing of EVs. A microarray assay can evaluate a large number of phenotypes by capturing EVs from biofluids. Ultimate detection occurs when each captured EV is individually counted and sized for each of the probes on the surface. Tens to hundreds of different probes can be used on a single microarray, 2. The SP-IRIS system does not require sample preparation or enrichment, 3. Detection of single binding events allows detection at concentrations at <10$^6$ nanoparticles/ml, dramatically improving the lower limit of detection, 4. SP-IRIS can be performed with small sample volumes (e.g., 25 µL of sample), 5. A single test can look for multiple biomarkers on the individual EVs captured by the primary probe on the sensor. For example, EVs are captured to the surface using primary probes immobilized on the sensor in a microarray format. The captured EVs can be counted and sized for all the primary probes. Then secondary probes can be introduced to the chip to co-localize two or more biomarkers on the individual EVs captured on the surface for every primary probe in the microarray.

Probes

Essentially any probe can be used to capture extracellular vesicles from a biological sample for quantification and/or characterization using an SP-IRIS system. In some embodiments, the capture probe(s) are an extracellular vesicle-specific probe such that extracellular vesicles can be captured from the biological sample, and other non-vesicle components of the biological sample can be washed away. It will be readily understood by one of skill in the art that a capture probe or extracellular vesicle-specific probe will bind to a marker or antigen that is exposed externally with respect to the extracellular vesicle. For example, the probe can bind to an extravesicular antigen of a transmembrane protein, or to an extravesicular component (e.g., vesicular associated RNA or protein). In some embodiments, the captured extracellular vesicles can be permeabilized or lysed to expose intravesicular components to the probes on the sensor. In such embodiments, SP-IRIS can be used to detect intra-exosomal constituents. Exemplary probes can include antibodies, antibody fragments, small molecules, compounds or other ligands.

As used herein the term "antibodies" can include polyclonal and monoclonal antibodies and antigen-binding derivatives or fragments thereof. Well known antigen binding fragments include, for example, single domain antibodies (dAbs; which consist essentially of single VL or VH antibody domains), Fv fragment, including single chain Fv fragment (scFv), Fab fragment, and F(ab')$_2$ fragment. Methods for the construction of such antibody molecules are well known in the art. As used herein, the term "antibody" refers to an intact immunoglobulin or to a monoclonal or polyclonal antigen-binding fragment with the Fc (crystallizable fragment) region or FcRn binding fragment of the Fc region. Antigen-binding fragments can be produced by recombinant DNA techniques or by enzymatic or chemical cleavage of intact antibodies. "Antigen-binding fragments" include, inter alia, Fab, Fab', F(ab')2, Fv, dAb, and complementarity determining region (CDR) fragments, single-chain antibodies (scFv), single domain antibodies, chimeric antibodies, diabodies and polypeptides that contain at least a portion of an immunoglobulin that is sufficient to confer specific antigen binding to the polypeptide. The terms Fab, Fc, pFc', F(ab') 2 and Fv are employed with standard immunological meanings [Klein, Immunology (John Wiley, New York, N.Y., 1982); Clark, W. R. (1986) The Experimental Foundations of Modern Immunology (Wiley & Sons, Inc., New York); Roitt, I. (1991) Essential Immunology, 7th Ed., (Blackwell Scientific Publications, Oxford)].

The term "polyclonal antibody" is defined herein as an antibody produced by several clones of B-lymphocytes as would be the case in a whole animal. The term "polyclonal antibody" usually refers to antibodies raised in immunized animals. A "monoclonal antibody" is defined herein as a cell line, whether within the body or in culture, that has a single clonal origin. Monoclonal antibodies are produced by a single clone of hybridoma cells, and are therefore a single species of antibody molecule. "Single chain antibody (Scfv)" is defined herein as a recombinant fusion protein wherein the two antigen binding regions of the light and heavy chains (Vh and Vl) are connected by a linking peptide, which enables the equal expression of both the light and heavy chains in a heterologous organism and stabilizes the protein. "F(Ab) fragment" is defined herein as fragments of immunoglobulin prepared by papain treatment. Fab fragments consist of one light chain linked through a disulphide bond to a portion of the heavy chain, and contain one antigen binding site. They can be considered as univalent antibodies. "F(Ab')$_2$ Fragment" is defined herein as the approximately 90 kDa protein fragment obtained upon pepsin hydrolysis of an immunoglobulin molecule N-terminal to the site of the pepsin attack. Contains both Fab fragments held together by disulfide bonds in a short section of the Fe fragment. "Fv Fragment" is defined herein as the N-terminal portion of a Fab fragment of an immunoglobulin molecule, consisting of the variable portions of one light chain and one heavy chain.

As used herein, the term "small molecule" refers to a chemical agent including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

As used herein, the term "drug" or "compound" refers to a chemical entity or biological product, or combination of chemical entities or biological products, administered to a person to treat or prevent to produce a biological action e.g., to control a disease or condition. The chemical entity or biological product is preferably, but not necessarily a low molecular weight compound, but can also be a larger compound, for example, an oligomer of nucleic acids, amino acids, or carbohydrates including, without limitation, proteins, oligonucleotides, ribozymes, DNAzymes, glycoproteins, siRNAs, lipoproteins, aptamers, and modifications and combinations thereof.

In certain embodiments it is contemplated that a secondary probe is used to further differentiate exosomal populations, extra-exosomal biomarkers or intra-exosomal biomarkers. Secondary probes are designed for discrimination of exosomal biomarker expression and/or other properties once the vesicles have been captured by the extracellular vesicle-specific probe(s) or capture probe(s).

While not necessary, in some embodiments it is contemplated that the secondary probe is labeled with a detectable moiety. Accordingly, when the SP-IRIS system is used in a multiplex format, it is contemplated that the plurality of secondary probes are each differentially labeled, e.g., with fluorescent moieties, for ease of discrimination of exosomal populations based on biomarker expression (e.g., internal or external).

In some embodiments, one or more of the reagents (e.g., an antibody reagent and/or nucleic acid probe) described herein can comprise a detectable moiety or label and/or comprise the ability to generate a detectable signal (e.g., by catalyzing reaction converting a compound to a detectable product). Detectable labels can comprise, for example, a light-absorbing dye, a fluorescent dye, or a radioactive label. Detectable labels, methods of detecting them, and methods of incorporating them into reagents (e.g., antibodies and nucleic acid probes) are well known in the art.

In some embodiments, detectable labels can include labels that can be detected by spectroscopic, photochemical, biochemical, immunochemical, electromagnetic, radiochemical, or chemical means, such as fluorescence, chemifluorescence, or chemiluminescence, or any other appropriate means. The detectable labels used in the methods described herein can be primary labels (where the label comprises a moiety that is directly detectable or that produces a directly detectable moiety) or secondary labels (where the detectable label binds to another moiety to produce a detectable signal, e.g., as is common in immunological labeling using secondary and tertiary antibodies). The detectable label can be linked by covalent or noncovalent means to the reagent. Alternatively, a detectable label can be linked such as by directly labeling a molecule that achieves binding to the reagent via a ligand-receptor binding pair arrangement or other such specific recognition molecules. Detectable labels can include, but are not limited to radioisotopes, bioluminescent compounds, chromophores, antibodies, chemiluminescent compounds, fluorescent compounds, metal chelates, and enzymes.

In other embodiments, the detection reagent is labeled with a fluorescent compound. In some embodiments, a detectable label can be a fluorescent dye molecule, or fluorophore including, but not limited to fluorescein, phycoerythrin, phycocyanin, o-phthaldehyde, fluorescamine, Cy3™, Cy5™, allophycocyanine, Texas Red, peridenin chlorophyll, cyanine, tandem conjugates such as phycoerythrin-Cy5™, green fluorescent protein, rhodamine, fluorescein isothiocyanate (FITC) and Oregon Green™, rhodamine and derivatives (e.g., Texas red and tetrarhodamine isothiocyanate (TRITC)), biotin, phycoerythrin, AMCA, CyDyes™, 6-carboxyfhiorescein (commonly known by the abbreviations FAM and F), 6-carboxy-2',4',7',4,7-hexachlorofiuorescein (HEX), 6-carboxy-4',5'-dichloro-2',7'-dimethoxyfiuorescein (JOE or J), N,N,N',N'-tetramethyl-6carboxyrhodamine (TAMRA or T), 6-carboxy-X-rhodamine (ROX or R), 5-carboxyrhodamine-6G (R6G5 or G5), 6-carboxyrhodamine-6G (R6G6 or G6), and rhodamine 110; cyanine dyes, e.g., Cy3, Cy5 and Cy7 dyes; coumarins, e.g. umbelliferone; benzimide dyes, e.g., Hoechst 33258; phenanthridine dyes, e.g., Texas Red; ethidium dyes; acridine dyes; carbazole dyes; phenoxazine dyes; porphyrin dyes; polymethine dyes, e.g., cyanine dyes such as Cy3, Cy5, etc.; BODIPY dyes and quinoline dyes; or derivatives thereof. In some embodiments, a detectable label can be a radiolabel including, but not limited to $^3$H, $^{125}$I, $^{35}$S, $^{14}$C, $^{32}$P, and $^{33}$P. In some embodiments, a detectable label can be an enzyme including, but not limited to horseradish peroxidase and alkaline phosphatase. An enzymatic label can produce, for example, a chemiluminescent signal, a color signal, or a fluorescent signal.

In some embodiments, a detectable label can be a spectral colorimetric label including, but not limited to colloidal gold or colored glass or plastic (e.g., polystyrene, polypropylene, and latex) beads.

Label-free Detection and Characterization of Extracellular Vesicles

Characterization of extracellular vesicles captured on a sensor and subjected to SP-IRIS analysis can be performed in a label-free format. In one embodiment, the extracellular vesicles captured and assessed using label-free detection methods are exosomes. In general, label-free detection permits one of skill in the art to assess the number of vesicles, and the morphological characteristics (e.g., size, shape, etc.) of the extracellular vesicle to be determined.

Methods for label-free detection generally involve providing a sensor comprising at least one extracellular vesicle-specific probe that will capture vesicles having a desired biomarker. For example, exosomes can be captured using exosome specific probes, such as an antibody that binds exosomal surface proteins CD63, CD9, CD81, at least one marker in Table 1 presented herein (e.g., at least 2, at least 3, at least 4, at least 5, at least 6, at least 7, at least 8, at least 9, at least 10, at least 15, at least 20, or more), or a combination thereof.

A sensor can be configured to comprise a plurality of extracellular-vesicle specific probes to capture at least two different populations of extracellular vesicles, such as populations of exosomes that express different exosomal surface markers. When using a plurality of extracellular-vesicle specific probes, it will be recognized that the location of the probes should be documented by location on the sensor. Thus, one of skill in the art can easily count the number of extracellular vesicles in a particular captured population and determine the average size and other morphological characteristics of the vesicles in each captured vesicle population (e.g., shape). One of skill in the art can also analyze the distribution pattern of captured vesicles in each sub-population as compared to a control sample, thereby determining if a shift in the number, shape or size of exosomes between the captured vesicle populations occurs as a result of e.g., progression of disease, treatment with a therapeutic agent or to determine if the patient will likely respond to treatment with a desired agent. This shift in exosomal populations can be assessed in a qualitative or quantitative manner.

The working Examples provided herein show the first demonstration of SP-IRIS techniques to detect exosomes from a biological sample, such as a blood sample.

Detection and Characterization of Extracellular Vesicles Using Labels

Also provided herein are methods of characterizing biomarker expression, both inside the extracellular vesicle and on the surface of the vesicle, using a second, labeled probe. Biomarkers that can be detected using labeled probes include nucleic acids (e.g., DNA, RNA, mRNA, miRNA etc.), lipids, and protein markers. The probe can be a complementary nucleic acid, a dye, an antibody or fragment thereof, or the like. Further information on particular probes, detectable labels and their use can be found in the section entitled "Probes." Specifically contemplated herein are the use of a plurality of differentially labeled probes that can be used to identify and characterize expression of a plurality of exosome biomarkers. In some embodiments, the plurality of probes are differentially labeled with nanoparticles comprising different sizes and/or shapes.

Detecting External Biomarkers: The detection of biomarkers on the surface or external to the extracellular vesicle can be performed prior to capture of the vesicles on the sensor or can be performed "on-chip" once the vesicles have been captured. To ensure the use of a minimal requirement for reagents to save cost, it is recognized that the on-chip analysis will require smaller amounts of the labeled probe and further will facilitate washing steps to remove unbound probe.

Typically, extra-vesicular markers are surface proteins, lipids or carbohydrate biomarkers.

Detecting and characterizing biomarker expression using labeled probes is straight-forward and can be performed by simply contacting captured vesicles with the probe, washing unbound probe away, and detecting the labeled probe using SP-IRIS. In some embodiments, a first, unlabeled antibody probe can be used to bind to an exosomal biomarker in combination with a second, labeled antibody that binds to the first unlabeled antibody for the purposes of detection.

Detecting Internal Biomarkers: Any intravesicular biomarker can be stained using the methods described herein. For example, protein biomarkers can be stained with labeled antibodies, aptamers or peptides; nucleic acids can be stained by complementary sequences labeled with a fluorophore (e.g., FISH assay); and lipids can be stained with dyes (e.g., DiO, DiA, DiL, DiD from Molecular Probes™, Eugene, Oreg.). The presence, amount or change in the level of a particular RNA (e.g., mRNA, miRNA), or DNA can be determined using the methods described herein. It is further contemplated herein that specific mutations, polymorphisms, or fusions can be detected using the methods described herein and can be used for the diagnosis of disease (e.g., a mutation in KRAS can be detected for the diagnosis of cancers, such as lung, colon, or pancreatic cancers; fusions in the ALK gene can be detected for the diagnosis of cancers, such as lung cancer). Probes, detectable labels and their use are described in the section entitled "Probes."

While not necessary, in some embodiments the detection of intra-vesicle, or intra-exosomal biomarkers can be performed following fixation and/or permeabilization of the vesicles. Fixation can be performed by any method known in the art and includes contacting the vesicles (e.g., captured vesicles, or pre-captured vesicles) with a fixative, such as glutaraldehyde, paraformaldehyde, formaldehyde, methanol, ethanol, acetone, formalin or a combination thereof. Some fixatives, such as methanol, ethanol, and acetone also act to permeabilize the vesicles. Permeabilization can be performed using electroporation, or through the use of detergents or enzymes (e.g., saponin, SDS, Triton-X100, Tween-20, NP40, Proteinase K, Streptolysin O, digitonin, among others).

Staining of intra-vesicular biomarkers can be performed via on-chip staining or can be performed following fixation and/or permeabilization on vesicles yet to be captured on the sensor. Post-processing of data can be performed to determine a number of output measures. For example, the heterogeneity of samples can be determined or the proportion of exosomes captured comprising certain biomolecules (e.g., lipids, proteins, nucleic acids etc.) or a combination of biomolecules. In addition, label-free data regarding size, shape and other characteristics can be correlated to fluorescence data relating to intravesicular biomarker abundance or expression.

The working Examples, particularly Example 3, described herein are the first demonstration of detecting intra-exosomal constituents using SP-IRIS techniques.

Reference Samples

In some embodiments, the characteristics of the extracellular vesicle (number, phenotype, or size, shape) and or expression levels of one or more biomarkers on an extracellular vesicle determined for a sample (e.g., output parameter) are compared to a reference. The terms "reference level," "reference sample," and "reference" are used interchangeably herein and refer to the measured output parameter in the test biological sample against which another sample is compared (i.e., obtained from an earlier time point, or obtained from an untreated sample).

A standard is useful for e.g., classifying the number, shape or size of captured extracellular vesicles that comprise a biomarker into a subset of the total captured extracellular vesicles. Typically, the standard in this embodiment is the size, shape or number of captured extracellular vesicles prior to treatment with a probe to detect the biomarker (i.e., the image obtained of captured extracellular vesicles prior to the phase shift that occurs upon contact of a biomarker probe). Also contemplated herein are defined ratios of biomarker-containing extracellular vesicles: total extracellular vesicles, which can then be compared to a ratio standard for the purposes of determining a diagnosis for disease. A standard is also useful for detecting a change in a measurable output parameter or a relative increase/decrease in the output parameter in a biological sample.

A standard serves as a reference level for comparison, such that samples can be normalized to an appropriate standard. An appropriate standard can be determined by one of skill in the art based on the output parameter to be measured and the application to which the methods described herein are to be used. For example, when the methods described herein are applied to test a candidate agent for a biological effect, the standard can be the biological sample prior to treatment with the candidate agent.

In one embodiment, a reference standard is obtained at an earlier time point (presumably prior to treatment) from the same biological sample that is to be tested or treated as described herein. Alternatively, a standard can be from the same biological sample following treatment as described herein.

In relation to a cellular diagnostic or prognostic assay for disease, a standard level can be obtained, for example, from a known biological sample from a different individual (e.g., not the individual being tested) that is substantially free of disease. In another embodiment, a standard level can be obtained from a known biological sample from the same individual outside of the captured extracellular vesicles (e.g., in a site known to be free of disease). A known sample can also be obtained by pooling samples from a plurality of individuals to produce a standard over an averaged population, wherein a standard represents an average level of an output parameter among a population of individuals (e.g., a population of individuals having the disease). Thus, the level of the output parameter in a standard obtained in this manner is representative of an average level of this parameter in a general population of individuals having the disease. A biological sample is compared to this population standard by comparing the output parameter from a sample relative to the population standard. Generally, a measurement of an output parameter that falls within a range determined in a specific population (e.g., in a population of subjects having disease) will indicate the presence of the disease, while a measurement that falls outside of the range will indicate that the individual does not have the disease. The converse is contemplated in cases where a standard is obtained from a population of subjects lacking the disease. It should be noted that there is often variability among individuals in a population, such that some individuals will have higher measurements for a given output parameter, while other individuals have lower measurements for the same parameter. However, one skilled in the art can make logical inferences on an individual basis regarding the detection and treatment of disease as described herein.

In one embodiment, the characteristics of captured vesicles on a particular sensor are compared to the characteristics of a reference sample of captured vesicles to determine if a phase shift occurs in the location or number of certain vesicle populations.

Screening Assays for Identifying and/or Testing Efficacy of Bioactive Agents

In one embodiment, the methods described herein can be used to screen candidate agents (e.g., small molecules, antibodies, inhibitory RNA etc.) for a biological effect. Typically, a biological sample comprising an extracellular vesicle is contacted with a candidate agent prior to, or following, capture of extracellular vesicles on an SP-IRIS sensor, and at least one output parameter is assessed using the methods described herein. The measurement of the output parameter is compared to a reference, such as the measurement of the output parameter prior to treatment with the candidate agent.

The term "candidate agent" is used herein to mean any agent that is being examined for a desired biological activity. A candidate agent can be any type of molecule, including, for example, a peptide, a peptidomimetic, a polynucleotide, or a small organic molecule, that one wishes to examine for the ability to modulate a desired activity. An "agent" can be any chemical, entity or moiety, including without limitation synthetic and naturally-occurring proteinaceous and non-proteinaceous entities. In some embodiments, an agent is nucleic acid, nucleic acid analogues, proteins, antibodies, peptides, aptamers, oligomer of nucleic acids, amino acids, or carbohydrates including without limitation proteins, oligonucleotides, ribozymes, DNAzymes, glycoproteins, siRNAs, lipoproteins, aptamers, and modifications and combinations thereof etc.

In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide agent or fragment thereof can be, for example, but not limited to; mutated proteins; therapeutic proteins; truncated proteins, wherein the protein is normally absent or expressed at lower levels in the cell. Proteins of interest can be selected from a group comprising; mutated proteins, genetically engineered proteins, peptides, synthetic peptides, recombinant proteins, chimeric proteins, antibodies, humanized proteins, humanized antibodies, chimeric antibodies, modified proteins and fragments thereof.

Candidate agents can be known to have a desired activity and/or property, or can be selected from a library of diverse compounds. Also included as candidate agents are pharmacologically active drugs, genetically active molecules, etc. Such candidate agents of interest include, for example, chemotherapeutic agents, hormones or hormone antagonists, growth factors or recombinant growth factors and fragments and variants thereof.

Candidate agents, such as chemical compounds, can be obtained from a wide variety of sources including libraries of synthetic or natural compounds, such as small molecule compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

In one embodiment of the screening method, compound libraries can be screened. Commercially available combinatorial small molecule drug libraries can be screened for a desired effect on a cell(s) using the imaging systems and methods well known in the art and/or as described herein. Combinatorial libraries can be obtained from commercially available sources including e.g., from Vitas-M Lab and Biomol International, Inc. A comprehensive list of compound libraries can be found at Broad Institute at Harvard University. Other chemical compound libraries such as those from of 10,000 compounds and 86,000 compounds from NIH Roadmap, Molecular Libraries Screening Centers Network (MLSCN) can also be used to supply candidate agents for the methods described herein.

With regard to intervention, any treatments which comprise a desired biological activity should be considered as candidates for human therapeutic intervention.

The present invention may be as defined in any one of the following numbered paragraphs:

1. A method for quantifying and/or characterizing extracellular vesicles from a biological sample, the method comprising: (a) contacting an SP-IRIS sensor comprising an extracellular vesicle-specific probe with a biological sample comprising at least one extracellular vesicle, thereby capturing the vesicle(s) on the sensor, (b) contacting the sensor having captured vesicle(s) with a secondary probe comprising a nanoparticle, and (c) imaging the nanoparticle using an SP-IRIS system, thereby quantifying and/or characterizing extracellular vesicles in the biological sample.

2. The method of paragraph 1, wherein the extracellular vesicle-specific probe and/or the secondary probe comprises an antibody.

3. The method of paragraph 1, wherein the extracellular vesicles comprise exosomes.

4. The method of paragraph 1, wherein the biological sample comprises a sample obtained from a subject.

5. The method of paragraph 4, wherein the sample obtained from a subject comprises a blood sample.

6. The method of paragraph 2, wherein the extracellular vesicle-specific antibody comprises an anti-CD63 antibody.

7. The method of paragraph 2, wherein the extracellular vesicle-specific antibody comprises an antibody directed against a biomarker.

8. The method of paragraph 1, wherein the nanoparticle comprises a gold particle.

9. The method of paragraph 1, wherein the captured extracellular vesicles are characterized by size and/or shape.

10. The method of paragraph 1, wherein the sensor further comprises at least one additional extracellular vesicle-specific antibody or a plurality of different extracellular vesicle-specific antibodies for multiplex detection.

11. The method of paragraph 10, wherein the plurality of extracellular vesicle-specific antibodies comprises at least 2, at least 5, at least 10, at least 50, at least 100 or more different extracellular vesicle-specific antibodies.

12. The method of paragraph 11, wherein the multiplex detection comprises a plurality of secondary probes.

13. The method of paragraph 12, wherein the plurality of secondary probes are differentially labeled.

14. The method of paragraph 13, wherein the plurality of secondary probes are differentially labeled with a plurality of nanoparticles that are differentiated by size and/or shape.

15. The method of paragraph 1, wherein the secondary probe binds to an intra-exosome marker.

16. An assay for determining the presence of a biomarker on extracellular vesicle(s) from a biological sample in a subject, the assay comprising the steps of: (a) contacting an SP-IRIS sensor comprising a first probe with a biological sample comprising at least one extracellular vesicle, thereby capturing the at least one vesicle on the sensor, (b) imaging the sensor to quantify and individually characterize bound extracellular vesicle(s), (c) contacting the sensor with a second probe comprising a secondary recognition probe that binds a biomarker on or inside the extracellular vesicle conjugated to a label, and (d) imaging the sensor and comparing the image to the image obtained in step (b), wherein a change in the signal imaged in (d) compared to the signal imaged in step (b) indicates the presence of the biomarker on the at least one vesicle.

17. The assay of paragraph 16, wherein the at least one extracellular vesicle comprises an exosome.

18. The assay of paragraph 16, wherein the first and/or second probe comprises an antibody.

19. The assay of paragraph 16, wherein the biological sample comprises a sample obtained from a subject.

20. The assay of paragraph 19, wherein the sample obtained from a subject comprises a blood sample.

21. The assay of paragraph 16, wherein the first probe comprises an anti-CD63 antibody.

22. The assay of paragraph 16, wherein the first and/or second antibody comprises an antibody directed against a biomarker.

23. The assay of paragraph 16, wherein the label comprises a nanoparticle, a fluorescent moiety, or a quantum dot.

24. The assay of paragraph 23, wherein the nanoparticle comprises a gold particle.

25. The assay of paragraph 16, wherein the captured extracellular vesicles are characterized by size and/or shape.

26. The assay of paragraph 16, wherein the sensor further comprises at least one additional extracellular vesicle-specific antibody or a plurality of different extracellular vesicle-specific antibodies for multiplex detection.

27. The assay of paragraph 21, wherein the plurality of extracellular vesicle-specific antibodies comprises at least 2, at least 5, at least 10, at least 50, at least 100 or more different extracellular vesicle-specific antibodies.

28. The assay of paragraph 16, wherein the biomarker is an intra-exosomal biomarker.

29. The assay of paragraph 16, wherein the biomarker is an extra-exosomal biomarker.

30. The assay of paragraph 16, wherein a plurality of secondary probes are used in step (c).

31. The assay of paragraph 30, wherein the plurality of secondary probes are differentially labeled.

32. The assay of paragraph 31, wherein the plurality of secondary probes are differentially labeled with a plurality of nanoparticles that are differentiated by size and/or shape.

33. A method for label-free detection of extracellular vesicles from a biological sample, the method comprising: (a) contacting an SP-IRIS sensor comprising an extracellular vesicle-specific probe with a biological sample comprising at least one extracellular vesicle, thereby capturing the vesicle(s) on the sensor, (b) imaging the nanoparticle using an SP-IRIS system, thereby detecting extracellular vesicles in the biological sample.

34. The method of paragraph 33, wherein the method further comprises determining the size, shape and/or number of the captured extracellular vesicles.

35. A method for detecting extra-vesicular biomarkers on an extracellular vesicle, the method comprising: (a) contacting an SP-IRIS sensor comprising an extracellular vesicle-specific probe with a biological sample comprising at least one extracellular vesicle, thereby capturing the vesicle(s) on the sensor, (b) contacting the sensor having captured vesicle(s) with a secondary probe directed to an extra-vesicular biomarker and further comprising a detectable moiety, and (c) imaging the detectable moiety using an SP-IRIS system, thereby detecting extra-vesicular biomarkers on the extracellular vesicles in the biological sample.

36. The method of paragraph 35, wherein the method is performed using a multiplex format.

37. The method of paragraph 36, wherein the multiplex format comprises the use of a plurality of secondary probes in step (b).

38. The method of paragraph 37, wherein the plurality of secondary probes are differentially labeled.

39. The method of paragraph 35, wherein the plurality of secondary probes are differentially labeled with a plurality of nanoparticles that are differentiated by size and/or shape.

40. A method for detecting intra-vesicular biomarkers inside an extracellular vesicle, the method comprising: (a) contacting an SP-IRIS sensor comprising an extracellular vesicle-specific probe with a biological sample comprising at least one extracellular vesicle, thereby capturing the vesicle(s) on the sensor, (b) fixing and/or permeabilizing the captured vesicles from step (a), (c) contacting the sensor having captured vesicle(s) with a secondary probe directed to an intra-vesicular biomarker and further comprising a detectable moiety, and (d) imaging the detectable moiety using an SP-IRIS system, thereby detecting intra-vesicular biomarkers on the extracellular vesicles in the biological sample.

41. A method for quantifying and/or characterizing extracellular vesicles from a biological sample, the method comprising: (a) contacting an SP-IRIS sensor comprising an extracellular vesicle-specific probe with a biological sample comprising at least one extracellular vesicle, thereby capturing the vesicle(s) on the sensor, (b) imaging the nanoparticle using an SP-IRIS system, thereby quantifying and/or characterizing extracellular vesicles in the biological sample.

42. A method for quantifying and/or characterizing extracellular vesicles from a biological sample, the method comprising: (a) contacting an SP-IRIS sensor comprising an extracellular vesicle-specific probe with a biological sample comprising at least one extracellular vesicle, thereby capturing the vesicle(s) on the sensor, (b) contacting the sensor having captured vesicle(s) with a secondary probe tagged with a fluorescent tag or a quantum dot, and (c) imaging the fluorescent tag or quantum dot using an SP-IRIS system, thereby quantifying and/or characterizing extracellular vesicles in the biological sample.

43. A method for quantifying and/or characterizing extracellular vesicles in a population that express a biomarker, the method comprising: (a) contacting a biological sample comprising at least one extracellular vesicle with one or more differentially labeled probes that bind one or more biomarkers, (b) contacting an SP-IRIS sensor comprising an extracellular vesicle-specific probe with the labeled biological sample of step (a), thereby capturing a population of extracellular vesicle(s) from the labeled biological sample of step (a) on the sensor, (c) imaging the captured extracellular vesicle(s) of step (b) using an SP-IRIS system, thereby quantifying and/or characterizing extracellular vesicles in the biological sample, (d) imaging the one or more differentially labeled probes using an SP-IRIS system, thereby quantifying and/or characterizing the extracellular vesicles labeled with the one or more differentially labeled probes in the biological sample, and (e) comparing the image obtained in step (d) with the image obtained in step (c) to quantify and/or characterize the extracellular vesicles expressing the one or more biomarkers in the population of extracellular vesicles captured in step (b).

EXAMPLES

Example 1: SP-IRIS Detection of Extracellular Vesicles

Detection System—the SP-IRIS (Single-Particle Interferometric Reflectance Imaging Sensor is a low-cost and compact biosensing platform that permits identification of individual captured nanoparticles based on size and shape. The reader acquires raw data by illuminating the sensor surface with a visible light LED source and images of the surface are captured using a 40× objective and a camera. The sensor surface is made with a highly reproducible semiconductor process that consists of a silicon dioxide layer on top of a silicon substrate. Interference of light reflected from the sensor surface is modified by the presence of particles producing a distinct signal that is captured by a conventional camera. A nanoparticle captured on the sensor appears as a dot on the image, and the size of the particle is calculated from the brightness of the particle at a specific wavelength using a forward model (Daaboul et al. (2010) *Nano Lett* 10:4727-4731). Size discrimination allows discernment from different nanoparticle populations bound to the surface, which also helps in reducing noise from particles that are non-specifically bound to the surface (i.e., debris from the environment or dust particles). In a SP-IRIS image, as many as a million distinct nanoparticles can be simultaneously detected. In addition, the SP-IRIS system has been optimized for ease of use through hardware and software automation that simplifies running the instrument to a few button clicks.

Extracellular Vesicle Imaging with SP-IRIS Platform—In one study, the SP-IRIS system has been shown to detect individual exosomes and EVs from cell culture supernatant of melanoma cell lines (WM35 and 1205Lu) and a breast cancer cell line (MCF-7). A SP-IRIS chip was functionalized with antibodies against CD63, neuropilin-2 (NRP-2) and caveolin-1. CD63 is a generic exosome specific marker (Simpson et al. (2008) *Proteomics* 8(19):4083-4099; Kowal et al. (2014) *Curr Opin Cell Biol* 29:116-125). NRP-2 has been shown to be malignancy-specific cell surface marker (Ellis, L M. (2006) *Mol Cancer Ther* 5(5):1099-1107). Caveolin-1 is a melanoma-specific exosomal marker that is detected only from exosomes secreted from tumor cells but not from other normal cells (Logozzi et al. (2009) *PLoS ONE* 4(4):e5219).

The results in FIG. 1 show that EVs were captured on the CD63, NRP-2, and Caveolin-1 probes for the melanoma cell lines (WM35 and 1205LU). The CD63 spot on the array indicates a uniform distribution of EVs that can be classified as exosomes, however NRP-2 and Caveolin-1 indicate a similar size distribution of particles in addition to larger EVs which could be classified as exosomes or microvesicles (data not shown). A microarray that can do phenotyping, sizing, and enumeration is a novel capability of the SP-IRIS platform.

Figure 2:
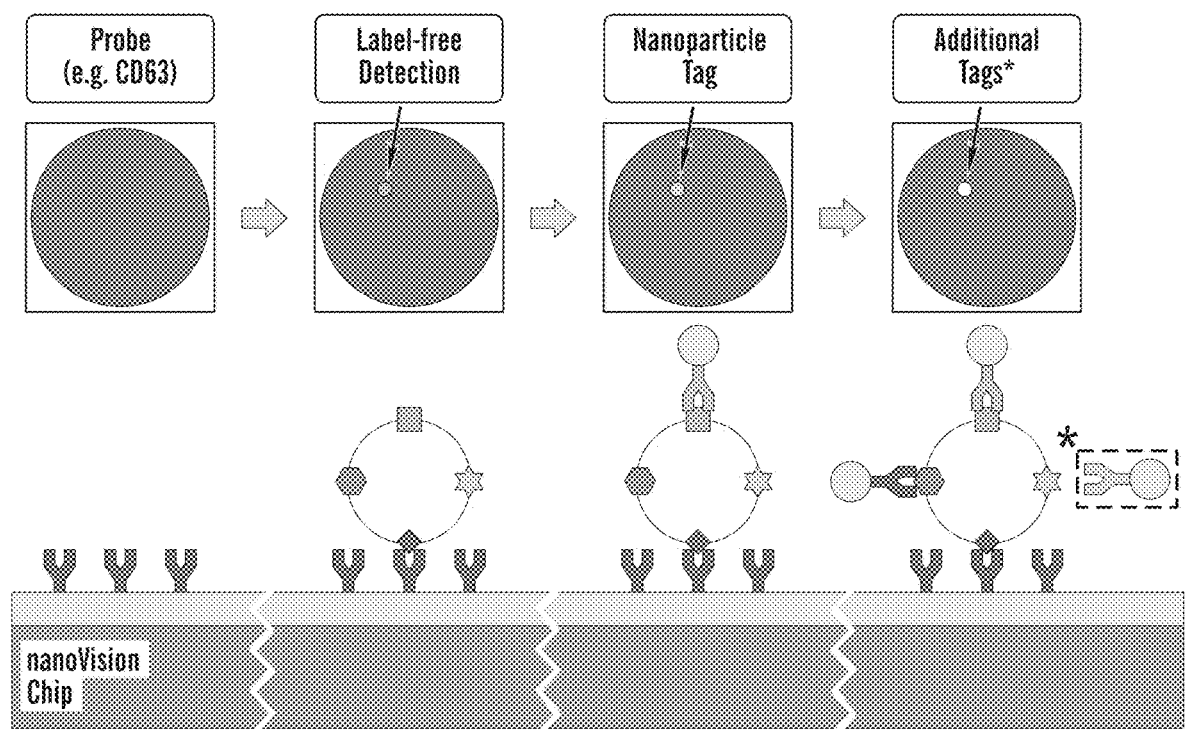
FIG. 2 shows a schematic representation of specific exosome detection with the SP-IRIS platform. Probes targeting different surface markers are immobilized on the chip. Particles are detected label-free. Orthogonal co-localization information can be determined via a nanoparticle tag. Additional tags can be used on the same exosome.
Figure 3A:
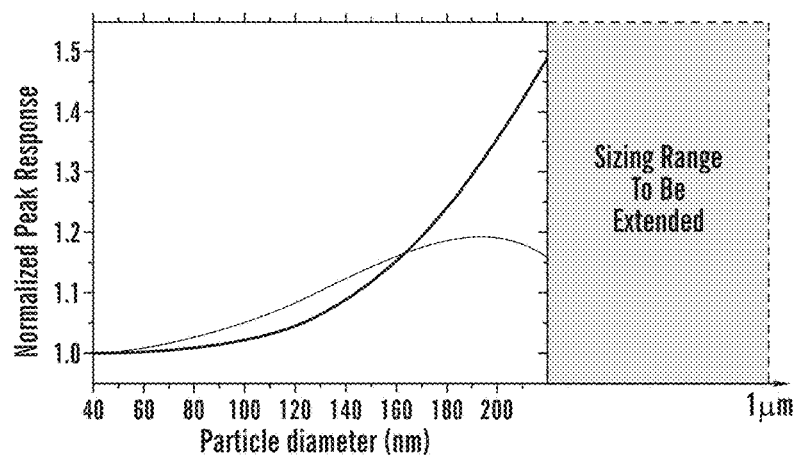
FIGS. 3A-3B.
Figure 3B:
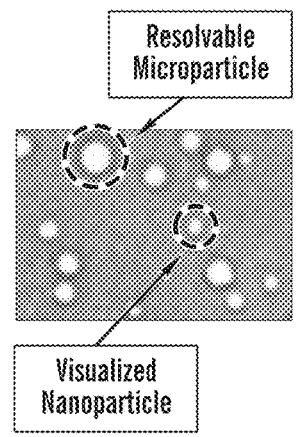

Co-localization of multiple markers on individual EVs—After capturing the EVs onto the microarray with the arrayed capture probes, a secondary antibody labeled with a gold nanoparticle is introduced to the sensor. The labeled antibody tag binds to exosomes that have the surface marker against the secondary antibody. The tagging of the exosome with the gold labeled antibody increases its size and therefore it appears brighter in the SP-IRIS image as illustrated in FIG. 2. This secondary labeling with immunogold tags is standard practice when looking at surface markers using electron microscopy (EM) (Yang et al. (2014) *PLoS ONE* 9(11): e110641; Kanwar et al. (2014) *Lab Chip* 14(11): 1891), which is low-throughput, expensive, and not scalable for wide adoption. In contrast, the SP-IRIS assay using the SP-IRIS platform allows one of skill in the art to perform similar capabilities as immunogold staining with EM at a fraction of the cost and in a high-throughput microarray format. Two surface markers can be co-localized by capturing the exosome on the surface with a primary probe and then detecting the second marker using a secondary probe tagged with e.g., a 4 0 nm gold particle. Co-localization of more than two surface markers can be achieved using nanoparticles that are smaller than e.g., 40 nm. Reducing the size of the label reduces the steric hindrance of binding of multiple gold nanoparticles against different surface markers. Therefore, by sequentially adding different secondary tags the size of the detected exosome sequentially increases if it has the surface protein marker on its surface. The step of size increase correlates to the size of the immunogold label and the surface concentration of the marker.

Sizing of nanoparticles, i.e. exosomes and microvesicles. The SP-IRIS platform was developed primarily for rapid and ultrasensitive detection of viral pathogens that have a diameter less than 200 nm, directly from complex samples like whole blood. The SP-IRIS system has been shown to count and accurately size particles from 70 nm to 200 nm (Daaboul et al. (2010) *Nano Lett*, supra; Yurt et al. (2012) *Nanoscale* 4(3):715). Recently, an assay was developed for the direct detection of Ebola and Marburg virus directly from whole blood with a sensitivity of <3.5×10$^3$ PFU/ml (Daaboul et al. (2014) *ACS Nano* 8(6):6047-6055). The SP-IRIS system can be used for the detection of exosomes and microvesicles associated with cancer and that range from 50 nm to 1 μm. Once the particles are larger than 1 μm they can be resolved by the microscope. For particles under the diffraction limit, which is around 800 nm, the size of the particle is inferred from the brightness of the particle response at different wavelengths.

The SP-IRIS system can be optimized for detecting sizes greater than 200 nm. To this end, polystyrene beads are immobilized on the SP-IRIS sensor chip with diameter sizes ranging from 50 nm to 1 μm at 100 nm steps. The response of the particles is acquired at different wavelengths. By using a combination of short and long wavelength LEDs, a system is developed that can count and size particles with a wide dynamic range of 50 nm to cell sized features.

Multiple marker co-localization on individual EVs through nanoparticle labeling. The SP-IRIS platform can be used to perform multiplexed detection of exosomes by arraying probes on the surface against different markers. Multiplexed detection quantifies the amount of exosomes for different protein markers; however, it does not necessarily validate the presence of multiple markers on the same exosome. The system can further be used to co-localize two or more surface biomarkers on individual exosomes captured on the surface by developing nanoparticle tagged secondary probes. This technique is conventionally performed through gold immunostaining and detected with electron microscopy (EM). EM is expensive, requires special sample preparation and specialized training, and is limited in throughput.

Figure 4:
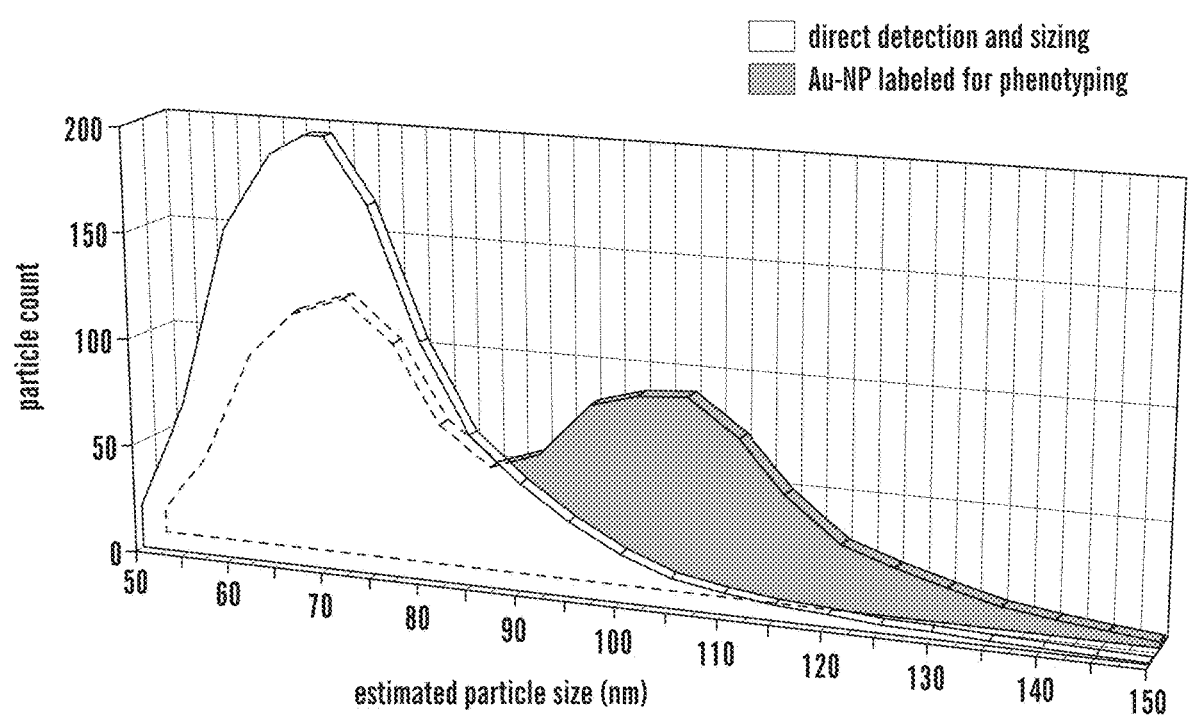
FIG. 4 Analysis of raw data, size vs. count, for label-free and gold-nanoparticle labeled populations.

In contrast, the SP-IRIS platform can visualize antibody probes tagged to 40 nm diameter gold nanoparticles with high signal-to-noise ratios. Exosomes captured with a CD63 probe on the sensor surface can be counted and sized using label-free detection (data not shown). Then, a secondary antibody (anti-NRP-2) tagged with 40 nm gold nanoparticles is flowed over the surface and the secondary antibody binds to the melanoma cell line derived exosomes, making the initially detected exosomes appear larger (data not shown). The sizing histogram in FIG. 4 also shows the resulting shift in the sizing histogram due to the binding of the secondary antibodies tagged with gold nanoparticles.

Labeling of the captured exosome with a secondary tag can be optimized, for example, the secondary label can be covalently bound to the carboxylate gold nanoparticle using well known EDC/NHS chemistry. The concentration of the labels and time of incubation can be optimized to ensure near 100% tagging efficiency. The tagging is confirmed with EM, which is the gold standard for immunogold detection.

Figure 5:
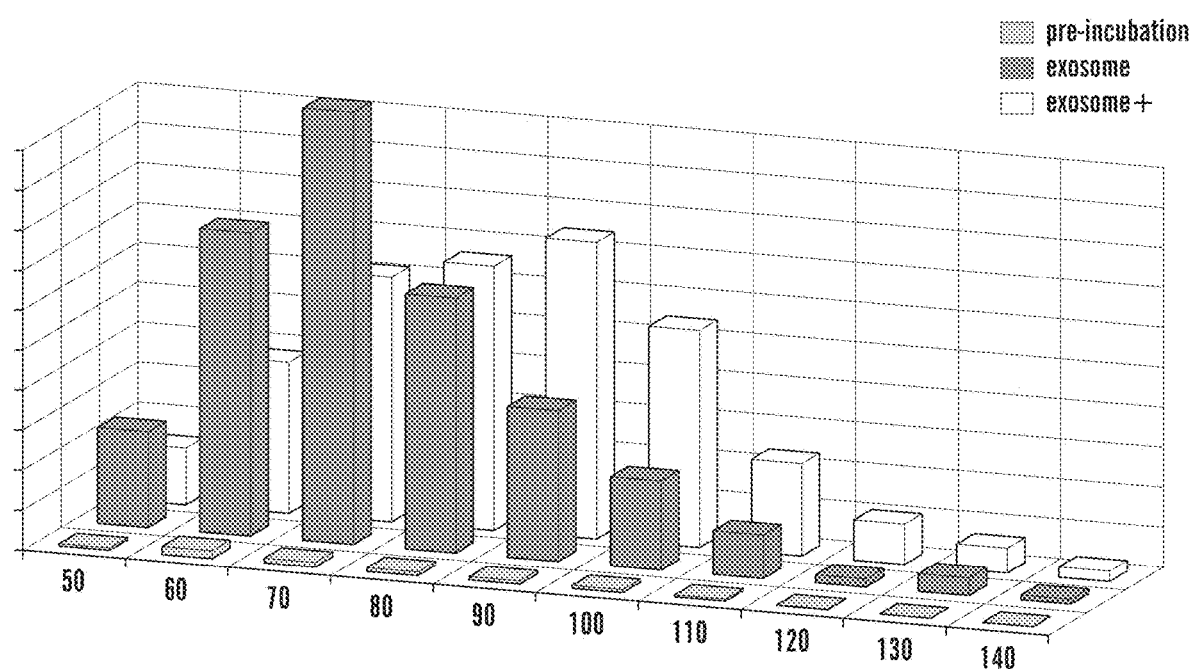
FIG. 5 shows an exemplary end point SP-IRIS detection experiment on exosomes. The size histogram of the captured exosomes (label free) and change in the size distribution after a secondary step of labeling with Au—NP demonstrates the ability to directly detect, size and phenotype.

Example 2: Optimization of Exosomal Nanovesicle Detection and Phenotyping Using SP-IRIS Data collected in dry conditions at the end point shown in FIG. 5 demonstrates the capability of the SP-IRIS technology in detecting exosome particles. Exosomes isolated from melanoma cell culture, and purified using ultracentrifugation, were captured on the surface using anti-CD63 antibody. Exosomes from a population with a size distribution of 60-100 nm in diameter are readily distinguishable from the background, however for their accurate quantification and size discrimination, further optimization can be performed. The same chips are later incubated with secondary antibodies labeled with Au—NP and imaged again under dry conditions. There is a significant shift in the size distribution showing that many of the previously captured, detected and sized exosomes are decorated with Au—NP indicating their affinity to the particular antibody—thus their phenotype. This exosomal phenotypic distinction capability of the SP-IRIS technology indicates that tumor secreted exosomes can be quantitatively detected by the double labeling of tumor-specific exosomal marker proteins such as NRP2 and Caveolin-1.

Experimental Design
Instrumentation of the SP-IRIS for Digital Detection of Exosomal Nanovesicles:

SP-IRIS detects nanometer-sized particles captured on antibody microarrays, and single particles are digitally counted with a resolution beyond that of state-of-the-art optical microscopy techniques. The analysis software extracts the size of the detected exosome particles within the 40 nm to 200 nm range with 5 nm accuracy of discrimination. Size discrimination is important for the characterization of the exosomes as the size distribution of the particle population may be indicative of sample heterogeneity and disease state. State-of-the-art technologies with size discrimination at this scale, such as electron microscopy, suffer from throughput and difficulty of use. The platform described herein enables phenotype characterization of the exosomes through capture on a multiplex microarray configuration and further verification with detection of gold nanoparticle tagged secondary antibodies. The platform is capable of simultaneous detection of the exosomes and gold nanoparticles, and the analysis software enables distinction of the two particle populations. In contrast to the state-of-the-art exosome analysis techniques, the platform exemplified herein provides high throughput analysis from low sample volumes with a low cost, easy to use and biocompatible system.

SP-IRIS Assay Optimization for Enumeration of Tumor-Specific Exosomes Using Exosomal Protein Markers:

Exosome enumeration and phenotyping: An SP-IRIS sensor consists of a silicon substrate with a thin oxide layer, which are each commercially fabricated. The sensors are then coated with a 3D polymeric surface which has been tested for detection of viral particles in complex media (human whole blood) and have shown great anti-fouling properties (22). S3 Flexarrayer™ from Scienion™ is then used to array capture probes on the surface. The probe immobilization on the sensor surface is optimized through testing different concentrations, buffer composition and pH. Optimized capture probes (e.g., antibodies) on the surface results in smooth protein spots and high capture probe density (>3 ng/mm$^2$). A dilution curve can be performed by spiking protein standards in PBS with 10% human serum albumin from nM to zero. The dilution curve tests the functionality of the antibodies on the sensor surface and indicates the sensitivity of the assay. If an antibody fails to bind the protein target more antibodies can be tested and optimized. The SP-IRIS sensor requires a detection antibody conjugated to a 40 nm gold nanoparticle to allow digital counting of molecular binding on the arrayed surface antibodies.

Neuropilin-2 (NRP2) is a transmembrane receptor protein that its expression level correlates with malignant progression in melanoma (4, 5). Caveolin-1 is an integral membrane protein involved in receptor-independent endocytosis (24-26) and melanoma-specific exosomal marker protein (7). These two exosomal marker proteins are ideal candidates for the quantitative detection of tumor-specific exosomes using the SP-IRIS (exosome phenotype differentiation). Antibodies of these exosome markers can be conjugated to commercially purchased carboxylated gold nanoparticles using standard EDC/NHS chemistry.

Platform Validation with Blood Samples:

To determine the assay reproducibility and detection sensitivity of the SP-IRIS technique in a context of clinical sample, the inventors used blood samples from normal healthy donors spiked with a known quantity of exosomes isolated from cancer cell lines. Exosomes are isolated from 1205Lu melanoma and MCF-7 breast cancer cells. The cancer cells are cultured for 32 h with exosome-free FBS media, then exosomes are isolated by a combination of ultracentrifugation and filtration adapted from traditional ultracentrifugation methods as described by Thery et al. (27). Exosome pellets are stored at −20° C. and yield is measured by BCA assay. Rabbit anti-NRP2 antibody (sc-5542, Santa Cruz™) and mouse anti-caveolin-1 antibody (sc-53564, Santa Cruz™) are used.

Optimization of SP-IRIS System:

Previously, the inventors have shown the ability to detect and size low-index nanoparticles as small as 60 nm in diameter. The inventors expect to improve the ability to extend to 40 nm size—requiring a ~4-fold improvement in the recognition of bright spots in the SP-IRIS image. Routine optimization of the SP-IRIS system e.g., by using improved image processing tools will be sufficient to visualize smaller particles. However, it may be desirable to have hardware solutions to increase the visibility of the nanoparticles (exosomes) for improved quantification and size discrimination. An exemplary method is the use of partial darkfield illumination (compared to matching illumination/collection). The inventors have found preliminary experiments and calculations to be encouraging (data not shown). Furthermore, previous experiments have been limited to single color image acquisition and the inventors are planning to implement multi-wavelength imaging and image registration.

Example 3: Detection and Characterization of Intra-Vesicular or Intra-Exosomal Biomarkers The methods described herein are further contemplated for detection and/or characterization of biomarkers within the extracellular vesicle (e.g., exosome). Exemplary methods for characterizing internal biomarkers (e.g., cargo) are provided herein.

Extracellular vesicles (e.g., exosomes) are captured on a sensor as described herein using an extracellular vesicle-specific probe, for example, at least one antibody, at least one peptide or at least one aptamers. In some embodiments, the vesicle population comprises 1-10,000 vesicles per spot on the sensor when characterizing internal markers.

In some embodiments, the captured vesicles are permeabilized to permit access of the second probe to the intravesicular biomarkers. In other embodiments, the captured vesicles are first fixed to the surface (e.g., with glutaraldehyde, paraformaldehyde, formaldehyde, methanol, ethanol, acetone, formalin or a combination thereof among others) prior to permeabilization. Permeabilization can be performed using electroporation, through the use of detergent (e.g., saponin, SDS, Triton-X100, Tween-20, NP40, Proteinase K, Streptolysin O, digitonin, among others) or organic solvents (e.g., methanol, ethanol, acetone, among others).

Staining of intra-vesicular biomarkers can be performed via on-chip staining. Any intravesicular biomarker can be stained using the methods described herein. For example, protein biomarkers can be stained with labeled antibodies, aptamers or peptides; nucleic acids can be stained by complementary sequences labeled with a fluorophore (e.g., FISH assay); and lipids can be stained with dyes (e.g., DiO, DiA, DiL, DiD from Molecular Probes™, Eugene, Oreg.). The presence, amount or change in the level of a particular RNA (e.g., mRNA, miRNA), or DNA can be determined using the methods described herein. It is further contemplated herein that specific mutations, polymorphisms, or fusions can be detected using the methods described herein and can be used for the diagnosis of disease (e.g., a mutation in KRAS can be detected for the diagnosis of cancers, such as lung, colon, or pancreatic cancers; fusions in the ALK gene can be detected for the diagnosis of cancers, such as lung cancer).

Post-processing of data can be performed to determine a number of output measures. For example, Label-free data regarding size and other characteristics can be correlated to fluorescence data relating to intravesicular biomarker abundance or expression. In another embodiment, the heterogeneity of samples can be determined or the proportion of exosomes captured comprising certain biomolecules (e.g., lipids, proteins, nucleic acids etc.) or a combination of biomolecules.

In one embodiment, a method for characterization of the internal cargo of captured vesicles comprises the steps of:

(i) capturing extracellular vesicles or exosomes on an SP-IRIS sensor comprising extracellular vesicle-specific probe(s),
(ii) optionally fixing the captured vesicles,
(iii) permeabilizing the captured vesicles,
(iv) staining the desired intravesicular biomarkers using a second probe, and
(v) optionally determining the number/size of vesicles comprising a particular biomarker, the heterogeneity of the sample, or the amount of biomarker located in an intravesicular compartment as compared to a reference.

In another embodiment, a method for characterization of the internal cargo of captured vesicles comprises the steps of:

(i) providing a sample of extracellular vesicles in a biofluid or buffer,
(ii) fixing and permeabilizing the extracellular vesicles in the biofluid or buffer,
(iii) staining the extracellular vesicles in the biofluid or buffer with at least a second probe,
(iv) capturing extracellular vesicles on an SP-IRIS sensor comprising extracellular vesicle-specific probe(s),
(v) determining the size and number of the captured vesicles using label-free methods of SP-IRIS as described herein,
(vi) measuring fluorescence of the second probe (or multiple colors if a plurality of differentially labeled probes is used),
(vii) correlated label-free data and fluorescence data to measure the heterogeneity of the samples, determine proportion of exosomes captured that comprise certain intravesicular biomarkers or a combination of biomarkers.

REFERENCES

1. Stoorvogel W, Kleijmeer M J, Geuze H J, Raposo G. The biogenesis and functions of exosomes. Traffic 2002; 3(5): 321-30.
2. Thery C, Zitvogel L, Amigorena S. Exosomes: composition, biogenesis and function. Nat Rev Immunol 2002; 2(8):569-79.
3. Valenti R, Huber V, Iero M, Filipazzi P, Parmiani G, Rivoltini L. Tumor-released microvesicles as vehicles of immunosuppression. Cancer Res 2007; 67(7):2912-5.
4. Rossi M, Tuck J, Kim O J, Panova I, Symanowski J T, Mahalingam M, et al. Neuropilin-2 gene expression correlates with malignant progression in cutaneous melanoma. Br J Dermatol 2014; 171(2):403-8.
5. Rushing E C, Stine M J, Hahn S J, Shea S, Eller M S, Naif A, et al. Neuropilin-2: a novel biomarker for malignant melanoma? Hum Pathol 2011; 43(3):381-9.
6. Daaboul G G, Vedula R S, Ahn S, Lopez C A, Reddington A, Ozkumur E, et al. LED-based interferometric reflectance imaging sensor for quantitative dynamic monitoring of biomolecular interactions. Biosens Bioelectron 2011; 26(5):2221-7.
7. Logozzi M, De Milito A, Lugini L, Borghi M, Calabro L, Spada M, et al. High levels of exosomes expressing CD63 and caveolin-1 in plasma of melanoma patients. PLoS One 2009; 4(4):e5219.
8. Keller S, Sanderson M P, Stoeck A, Altevogt P. Exosomes: from biogenesis and secretion to biological function. Immunol Lett 2006; 107(2):102-8.

9. van der Pol E, Boing A N, Harrison P, Sturk A, Nieuwland R. Classification, functions, and clinical relevance of extracellular vesicles. Pharmacol Rev 2012; 64(3):676-705.
10. Johnstone R M, Bianchini A, Teng K. Reticulocyte maturation and exosome release: transferrin receptor containing exosomes shows multiple plasma membrane functions. Blood 1989; 74(5): 1844-51.
11. Huotari J, Helenius A. Endosome maturation. Embo J 2011; 30(17):3481-500.
12. Thery C, Ostrowski M, Segura E. Membrane vesicles as conveyors of immune responses. Nat Rev Immunol 2009; 9(8):581-93.
13. Booth A M, Fang Y, Fallon J K, Yang J M, Hildreth J E, Gould S J. Exosomes and HIV Gag bud from endosome-like domains of the T cell plasma membrane. J Cell Biol 2006; 172(6):923-35.
14. Bobrie A, Colombo M, Raposo G, Thery C. Exosome secretion: molecular mechanisms and roles in immune responses. Traffic 2011; 12(12):1659-68.
15. Hill H D, Mirkin C A. The bio-barcode assay for the detection of protein and nucleic acid targets using DTT-induced ligand exchange. Nat Protoc 2006; 1(1):324-36.
16. Nam J M, Thaxton C S, Mirkin C A. Nanoparticle-based bio-bar codes for the ultrasensitive detection of proteins. Science 2003; 301(5641): 1884-6.
17. Zhou W J, Chen Y, Corn R M. Ultrasensitive microarray detection of short RNA sequences with enzymatically modified nanoparticles and surface plasmon resonance imaging measurements. Anal Chem 2011; 83(10):3897-902.
18. Du Y, Chen C, Li B, Zhou M, Wang E, Dong S. Layer-by-layer electrochemical biosensor with aptamer-appended active polyelectrolyte multilayer for sensitive protein determination. Biosens Bioelectron 2010; 25(8): 1902-7.
19. Maehashi K, Katsura T, Kerman K, Takamura Y, Matsumoto K, Tamiya E. Label-free protein biosensor based on aptamer-modified carbon nanotube field-effect transistors. Anal Chem 2007; 79(2):782-7.
20. Choi N W, Kim J, Chapin S C, Duong T, Donohue E, Pandey P, et al. Multiplexed detection of mRNA using porosity-tuned hydrogel microparticles. Anal Chem 2012; 84(21):9370-8.
21. Yurt A, Daaboul G G, Connor J H, Goldberg B B, Unlu M S. Single nanoparticle detectors for biological applications. Nanoscale 2012; 4(3):715-26.
22. Daaboul G G, Lopez C A, Chinnala J, Goldberg B B, Connor J H, Unlu M S. Digital sensing and sizing of vesicular stomatitis virus pseudotypes in complex media: a model for ebola and marburg detection. ACS Nano 2014; 8(6):6047-55.
23. Properzi F, Logozzi M, Fais S. Exosomes: the future of biomarkers in medicine. Biomark Med 2013; 7(5):769-78.
24. Shatz M, Liscovitch M. Caveolin-1: a tumor-promoting role in human cancer. Int J Radiat Biol 2008; 84(3):177-89.
25. Tang Z, Scherer P E, Okamoto T, Song K, Chu C, Kohtz D S, et al. Molecular cloning of caveolin-3, a novel member of the caveolin gene family expressed predominantly in muscle. J Biol Chem 1996; 271(4):2255-61.
26. Williams T M, Lisanti M P. The caveolin proteins. Genome Biol 2004; 5(3):214.
27. Thery C, Amigorena S, Raposo G, Clayton A. Isolation and characterization of exosomes from cell culture supernatants and biological fluids. Curr Protoc Cell Biol 2006; Chapter 3: Unit 3 22.

The invention claimed is:
1. A method for quantifying and/or characterizing particles from a biological sample, the method comprising:
  (a) contacting a sensor of a single particle interferometric reflectance imaging sensor (SP-IRIS) system comprising one or more particle-specific probes with a biological sample comprising at least one particle, thereby capturing particle(s) on the sensor,
  (b) contacting the sensor of the SP-IRIS system having the captured particle(s) with secondary probes tagged with fluorescent tags and/or quantum dots, wherein the secondary probes comprise a plurality of differentially labeled probes, each providing for detection of a particular biomarker of a plurality of biomarkers, and
  (c) imaging the fluorescent tags and/or quantum dots using the SP-IRIS system and co-localizing two or more biomarkers on and/or within each of one or more individual particle(s) of the particle(s) captured on the surface of the SP-IRIS sensor, thereby quantifying and/or characterizing expression of the plurality of biomarkers of the particles in the biological sample.
2. A method for quantifying and/or characterizing expression of biomarkers by a population of particles, the method comprising:
  (a) contacting a biological sample comprising particles with one or more differentially labeled probes that bind one or more biomarkers,
  (b) contacting a sensor of a single particle interferometric imaging sensor (SP-IRIS) system comprising one or more particle-specific probes with the labeled biological sample of step (a), thereby capturing a population of particles from the labeled biological sample of step (a) on the sensor of the SP-IRIS system,
  (c) imaging the captured particles of step (b) using the SP-IRIS system, thereby quantifying and/or characterizing the captured particles,
  (d) imaging the one or more differentially labeled probes using the SP-IRIS system, thereby quantifying and/or characterizing the at least a portion of the captured particles having been labeled with the one or more differentially labeled probes in the biological sample, and
  (e) comparing the image obtained in step (d) with the image obtained in step (c) to quantify and/or characterize expression of the one or more biomarkers in the population of particles captured in step (b).
3. The method of claim 1, wherein step (c) comprises measuring fluorescence of the tagged secondary probes at multiple colors.
4. The method of claim 1, wherein the plurality of biomarkers comprise an intra-vesicular biomarker and the method comprises fixing and/or permeabilizing the captured particle(s).
5. The method of claim 1, wherein the plurality of biomarkers comprise one or more members selected from the group consisting of nucleic acids, lipids, and protein markers.
6. The method of claim 1, wherein the plurality of biomarkers comprise one or more members selected from the group consisting of Neuropilin-2 (NRP2) and Caveolin-1.

7. The method of claim 1, wherein the plurality of biomarkers comprise one or more members selected from the group consisting of EGFRvIII, EGFR, Her2/neu, EpCam, and Tspan8.

8. The method of claim 1, wherein the plurality of biomarkers comprise one or more members selected from the group consisting of CD24, CD63, CD151, CD 147, CD104, and CD24.

9. The method of claim 1, wherein the plurality of biomarkers comprise L1CAM.

10. The method of claim 1, wherein the secondary probes comprise a complementary nucleic acid and/or an antibody or fragment thereof.

11. The method of claim 1, wherein the one or more particle-specific probes comprise a plurality of probes immobilized on the sensor of the SP-IRIS system in a microarray format.

12. The method of claim 1, wherein the one or more particle-specific probes comprise an antibody that binds to one or more members selected from the group consisting of CD63, CD9, and CD81.

13. The method of claim 2, wherein the one or more biomarkers comprise a plurality of biomarkers and the method comprises co-localizing two or more biomarkers on individual particles captured on the sensor of the SP-IRIS system.

14. The method of claim 2, comprising determining a number and/or size of particles comprising a particular biomarker of the one or more biomarkers.

15. The method of claim 2, comprising determining a proportion of the captured particles that comprise certain biomarkers or a combination of biomarkers of the one or more biomarkers.

16. The method of claim 2, wherein the differentially labeled probes comprise fluorescently tagged probes and step (d) comprises measuring fluorescence at multiple colors.

17. The method of claim 2, wherein the one or more biomarkers comprise an intra-vesicular biomarker and the method comprises fixing and/or permeabilizing the captured particles.

18. The method of claim 2, wherein the one or more biomarkers comprise one or more members selected from the group consisting of nucleic acids, lipids, and protein markers.

19. The method of claim 2, wherein the plurality of biomarkers comprise one or more members selected from the group consisting of Neuropilin-2 (NRP2) and Caveolin-1.

20. The method of claim 2, wherein the plurality of biomarkers comprise one or more members selected from the group consisting of EGFRvIII, EGFR, Her2/neu, EpCam, and Tspan8.

21. The method of claim 2, wherein the plurality of biomarkers comprise one or more members selected from the group consisting of CD24, CD63, CD151, CD147, CD104, and CD24.

22. The method of claim 2, wherein the plurality of biomarkers comprise L1CAM.

23. The method of claim 2, wherein the differentially labeled probes comprise a complementary nucleic acid and/or an antibody or fragment thereof.

24. The method of claim 2, wherein the one or more particle-specific probes comprise a plurality of probes immobilized on the sensor of the SP-IRIS system in a microarray format.

25. The method of claim 2, wherein the one or more particle-specific probes comprise an antibody that binds to one or more members selected from the group consisting of CD63, CD9, and CD81.

26. The method of claim 1, wherein the captured particle(s) comprise nanovesicles.

27. The method of claim 1, wherein the captured particle(s) comprise viral particles.

28. The method of claim 1, wherein the captured particle(s) comprise extracellular vesicles.

29. The method of claim 1, wherein the captured particle(s) comprise one or more particle(s) each having a diameter less than 200 nm.

30. The method of claim 2, wherein the captured particles comprises nanovesicles.

31. The method of claim 2, wherein the captured particles comprises viral particles.

32. The method of claim 2, wherein the captured particles comprises extracellular vesicles.

33. The method of claim 2, wherein the captured particles comprises one or more particle(s) each having a diameter less than 200 nm.

* * * * *